(12) United States Patent
Tada et al.

(10) Patent No.: US 10,743,905 B2
(45) Date of Patent: Aug. 18, 2020

(54) MEDICAL DEVICE AND TREATMENT METHOD

(71) Applicant: TERUMO KABUSHIKI KAISHA, Shibuya-ku, Tokyo (JP)

(72) Inventors: Yuichi Tada, Kanagawa (JP); Mizuho Hirao, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 69 days.

(21) Appl. No.: 15/689,186

(22) Filed: Aug. 29, 2017

(65) Prior Publication Data
US 2018/0055535 A1     Mar. 1, 2018

(30) Foreign Application Priority Data

Aug. 30, 2016   (JP) .................................. 2016-167738

(51) Int. Cl.
*A61B 17/3207* (2006.01)
*A61M 25/00* (2006.01)
(Continued)

(52) U.S. Cl.
CPC ................ *A61B 17/320725* (2013.01); *A61B 17/320758* (2013.01); *A61M 25/0023* (2013.01); *A61M 29/02* (2013.01); *A61B 17/221* (2013.01); *A61B 17/32053* (2013.01); *A61B 2017/00685* (2013.01); *A61B 2017/2212* (2013.01);
(Continued)

(58) Field of Classification Search
CPC ........... A61B 2017/32053; A61B 2017/22039; A61B 2017/22079; A61B 2017/2212; A61B 2017/320766; A61B 2017/320775; A61B 2017/320758; A61B 17/32075; A61B 17/320758; A61B 17/320016;
(Continued)

(56) References Cited

U.S. PATENT DOCUMENTS

| 8,062,258 B2 | 11/2011 | Demarais et al. |
| 2013/0096587 A1 | 4/2013 | Smith et al. |
| 2015/0282833 A1* | 10/2015 | Yoon ................ A61B 17/32002 606/114 |

FOREIGN PATENT DOCUMENTS

| JP | H06-090958 A | 4/1994 |
| JP | 2014-533147 A | 12/2014 |

OTHER PUBLICATIONS

Office Action (Notice of Reasons for Refusal) dated Jan. 27, 2020, by the Japanese Patent Office in corresponding Japanese Patent Application No. 2016-167738 and an English Translation of the Office Action. (4 pages).

* cited by examiner

Primary Examiner — Tiffany Legette
(74) Attorney, Agent, or Firm — Buchanan Ingersoll & Rooney PC

(57) ABSTRACT

A medical device for removing an object within a living body lumen includes a rotatable tubular driven shaft having a leading-out hole opening in a proximal portion of the driven shaft, a cutting unit disposed on a distal side of the driven shaft, the cutting unit cutting an object while rotating together with the driven shaft, and a suction tubular body having a distal portion and a proximal portion, the distal portion of the suction tubular body being located within the driven shaft, the proximal portion of the suction tubular body being located outside the driven shaft and extending in a direction of separating from the driven shaft outward in a radial direction of the driven shaft.

20 Claims, 20 Drawing Sheets

(51) Int. Cl.
*A61M 29/02* (2006.01)
*A61B 17/00* (2006.01)
*A61B 17/22* (2006.01)
*A61B 17/3205* (2006.01)
*A61B 17/221* (2006.01)

(52) U.S. Cl.
CPC ............... *A61B 2017/22039* (2013.01); *A61B 2017/22079* (2013.01); *A61B 2017/320766* (2013.01); *A61B 2017/320775* (2013.01); *A61B 2217/005* (2013.01)

(58) Field of Classification Search
CPC .... A61B 17/32002; A61B 2017/22078; A61B 2017/320733
See application file for complete search history.

710

MEDICAL DEVICE AND TREATMENT METHOD

CROSS-REFERENCES TO RELATED APPLICATIONS

This application claims priority to Japanese Application No. 2016-167738 filed on Aug. 30, 2016, the entire content of which is incorporated herein by reference.

FIELD OF THE INVENTION

The present disclosure generally relates to a medical device and a treatment method for cutting an object from an inner wall surface of a living body lumen.

BACKGROUND DISCUSSION

Methods for treating a stenosis resulting from plaque, a thrombus, or the like within a blood vessel include a method involving expanding the blood vessel by a balloon, a method involving indwelling a stent in a mesh form or a coil form within the blood vessel as a support for the blood vessel, and the like. However, it is difficult to apply these methods when the plaque in the stenosis part is calcified and hardened, or occurs at a branching portion of blood vessels. A method enabling treatment even in such cases is atherectomy that cuts a stenosis object such as a plaque, a thrombus, or the like.

U.S. Pat. No. 8,062,258, for example, describes, as a device for atherectomy, a catheter provided with a mechanism for conveying a cut object. The catheter has a long rotating shaft within a tubular body, and spiral projections and depressions are provided on an outer circumference of the rotating shaft. The rotating shaft is rotatable within the catheter. When the rotating shaft is rotated in the catheter, an object located in the spiral depressions is conveyed in an axial direction within the catheter while pushed by the projections.

SUMMARY

When the object is conveyed by the catheter described in the patent noted above the object receiving a force from the rotating shaft rotates within the catheter. Therefore, the object within the catheter moves to a proximal side while describing a spiral within the catheter. Hence, the conveyance distance of the conveyed object within the catheter is increased, and a quantity that can be conveyed is decreased.

The disclosure here provides a medical device and a treatment method that can effectively remove an object within a living body lumen.

A medical device according to the present disclosure includes: a rotatable tubular driven shaft possessing a proximal portion and a distal portion, with the proximal portion of the driven shaft including a leading-out hole; a cutting unit disposed at the distal portion of the driven shaft and rotatable together with the driven shaft to cut the object while rotating together with the driven shaft; and a suction tubular body possessing a distal portion and a proximal portion. The distal portion of the suction tubular body is located within the driven shaft, and the proximal portion of the suction tubular body is located outside the driven shaft and extends in a direction projecting outward away from the driven shaft in a radial direction of the driven shaft.

A treatment method according to the present disclosure comprises: inserting a distal portion of a driven shaft into the living body lumen to position a cutting unit, provided at a distal portion of the driven shaft, adjacent the lesioned part, with the driven shaft also including an interior in which is positioned a suction tubular body, and the suction tubular body including an interior that communicates with an open distal end of the suction tubular body; cutting the object within the living body lumen while rotating the cutting unit so that the object is cut by the rotating cutting unit; and rotating the suction tubular body during the cutting of the object to create a suction force in the interior of the suction tubular body. The suction force in the interior of the suction tubular body communicates with the interior of the driven shaft to draw the object into the interior of the driven shaft. The method also includes extracting the driven shaft from within the living body lumen.

According to another aspect, a medical device for removing an object within a living body lumen comprises: a driven shaft configured to be connected to a driving unit to rotate the driven shaft, wherein the driven shaft includes an interior communicating with an open distal end of the driven shaft and open proximal end of the driven shaft. The driven shaft includes a leading-out hole passing through the driven shaft to communicate the interior of the driven shaft to outside of the driven shaft, the leading-out hole being spaced distally from the open proximal end of the driven shaft. The medical device also includes a suction tubular body possessing a distal portion, a proximal portion, a distal open end and an open proximal end, with the distal portion of the suction tubular body being located within the interior of the driven shaft, and a part of the suction tubular body passing through the leading out hole so that the proximal portion of the suction tubular body is positioned at the outside of the driven shaft, the proximal portion of the suction tubular body extending in a direction in which the proximal portion of the suction tubular body is angled relative to the driven shaft so that the proximal portion of the suction tubular body separates at progressively greater distances from the driven shaft toward the open proximal end of the suction tubular body. The open distal end of the suction tubular body communicates with the interior of the driven shaft, and the suction tubular body is rotatable to create a suction force in the interior of the suction tubular body that communicates with the interior of the driven shaft by way of the open distal end of the suction tubular body so that the suction force draws the object into the interior of the drive shaft.

In the medical device and the treatment method configured as described above, when the driven shaft is rotated to rotate the cutting unit, the proximal portion of the suction tubular body whirls. Thereby, a centrifugal force directed outward in the radial direction of the rotating driven shaft acts on matter within the proximal portion of the suction tubular body, and a suction force directed to the proximal side occurs within the suction tubular body. Therefore, the object can be conveyed by making the suction force act on the inside of the driven shaft using the rotation of the driven shaft that rotates the cutting unit. Thus, the object within the living body lumen can be removed effectively.

DETAILED DESCRIPTION

Figure 1:
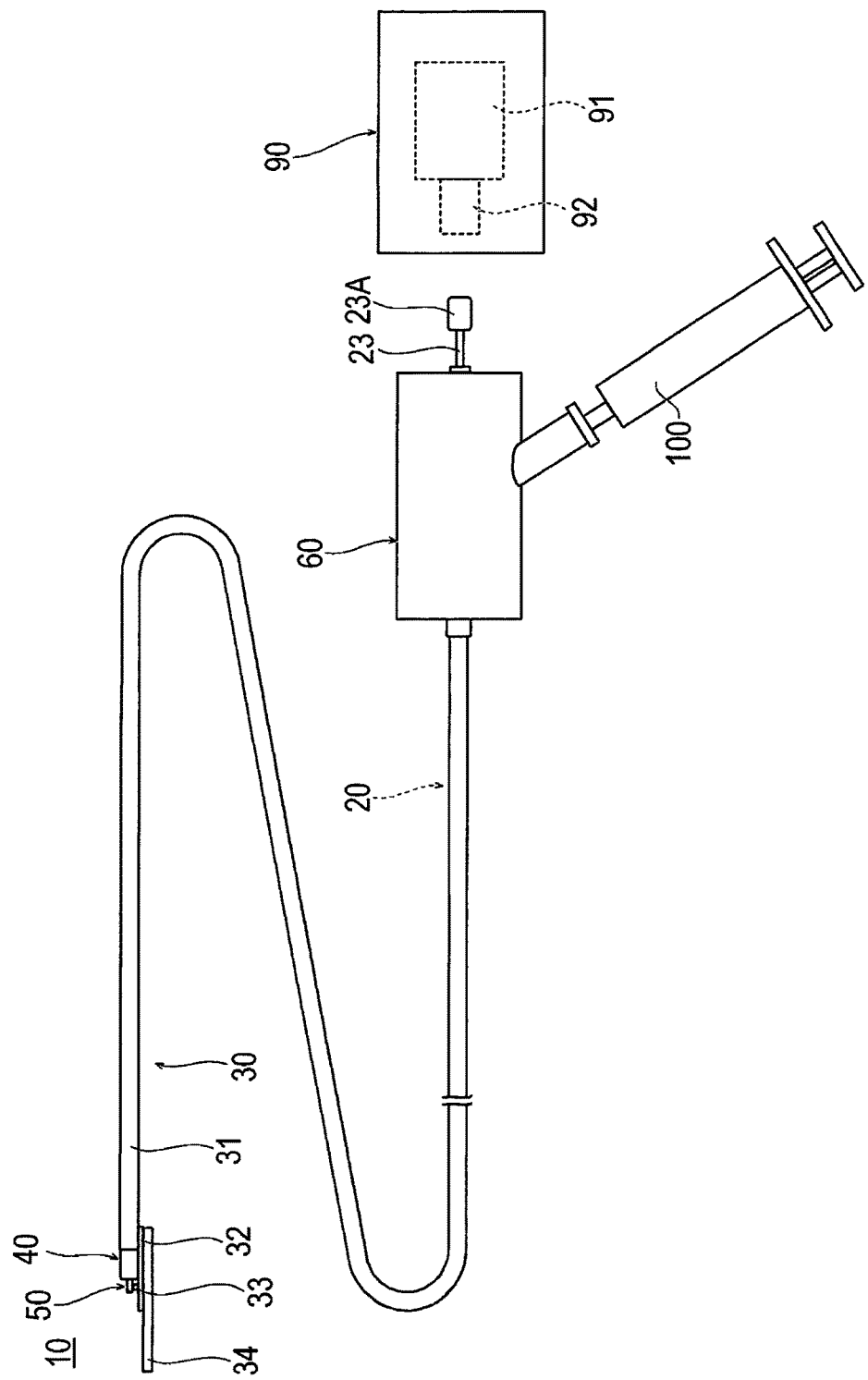
FIG. 1 is a plan view illustrating a medical device according to a first embodiment.

Set forth below with reference to the accompanying drawings is a detailed description of embodiments of a medical device and a treatment method representing examples of the inventive medical device and a treatment method disclosed here. Dimensional ratios in the drawings may be exaggerated and different from actual ratios for the convenience of description.

First Embodiment

A medical device 10 according to a first embodiment is configured to be inserted into a blood vessel and used for a treatment of (e.g., destroying and removing) a thrombus in a case of acute lower limb ischemia or deep venous thrombosis. In the present specification, a side of the device which is inserted into a blood vessel will be referred to as a "distal side" or "distal end," and a hand side of the device which is operated by the user will be referred to as a "proximal side" or "proximal end." The object to be removed is not necessarily limited to a thrombus, plaque, or a calcified lesion, but all objects that can be present within living body lumens can apply.

Figure 2:
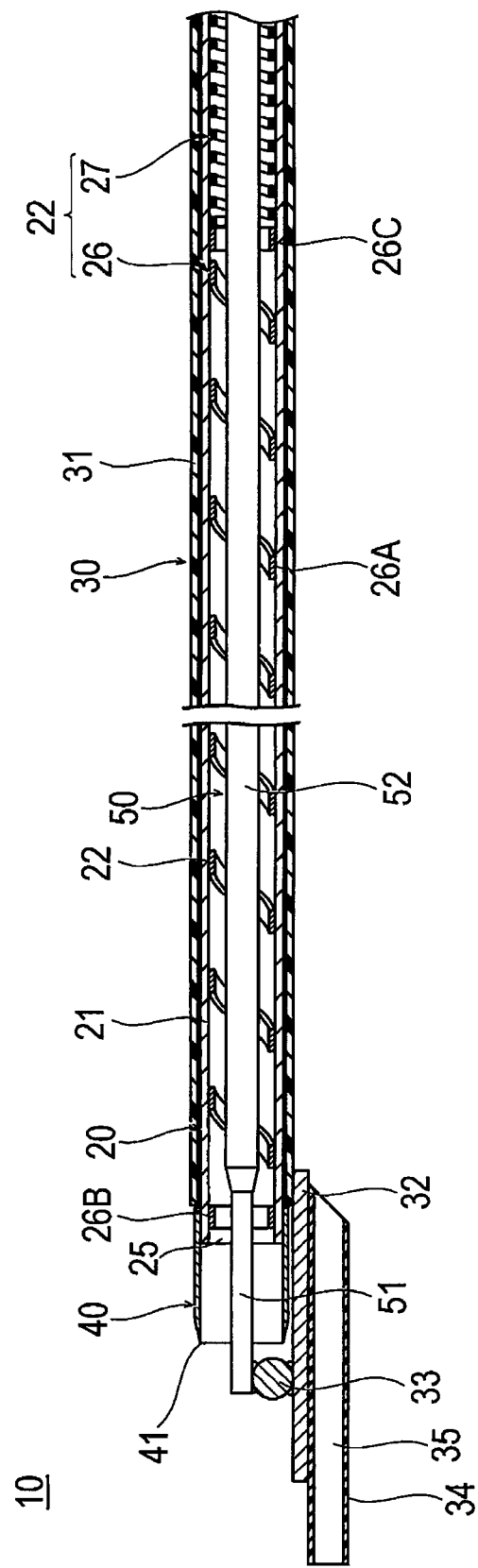
FIG. 2 is a sectional view illustrating a distal portion of the medical device.
Figure 3:
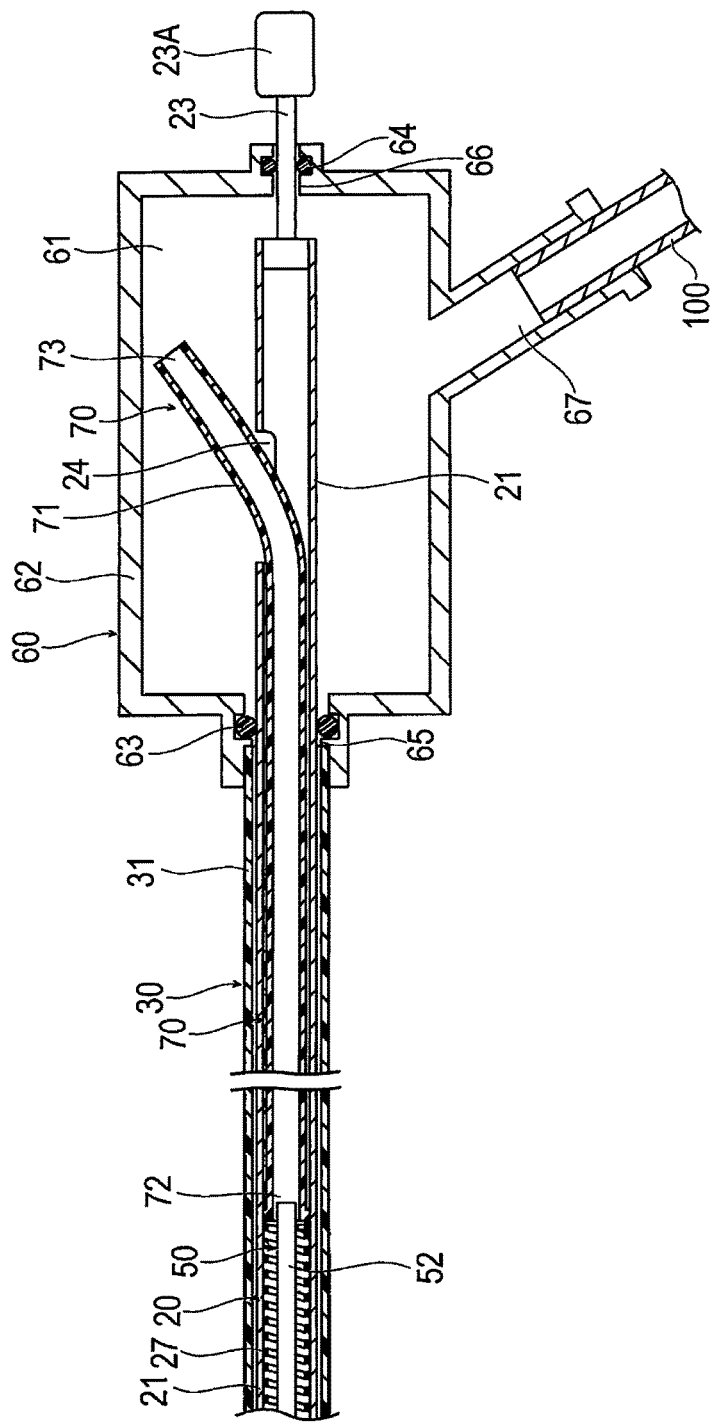
FIG. 3 is a sectional view illustrating a proximal portion of the medical device.
Figure 4:
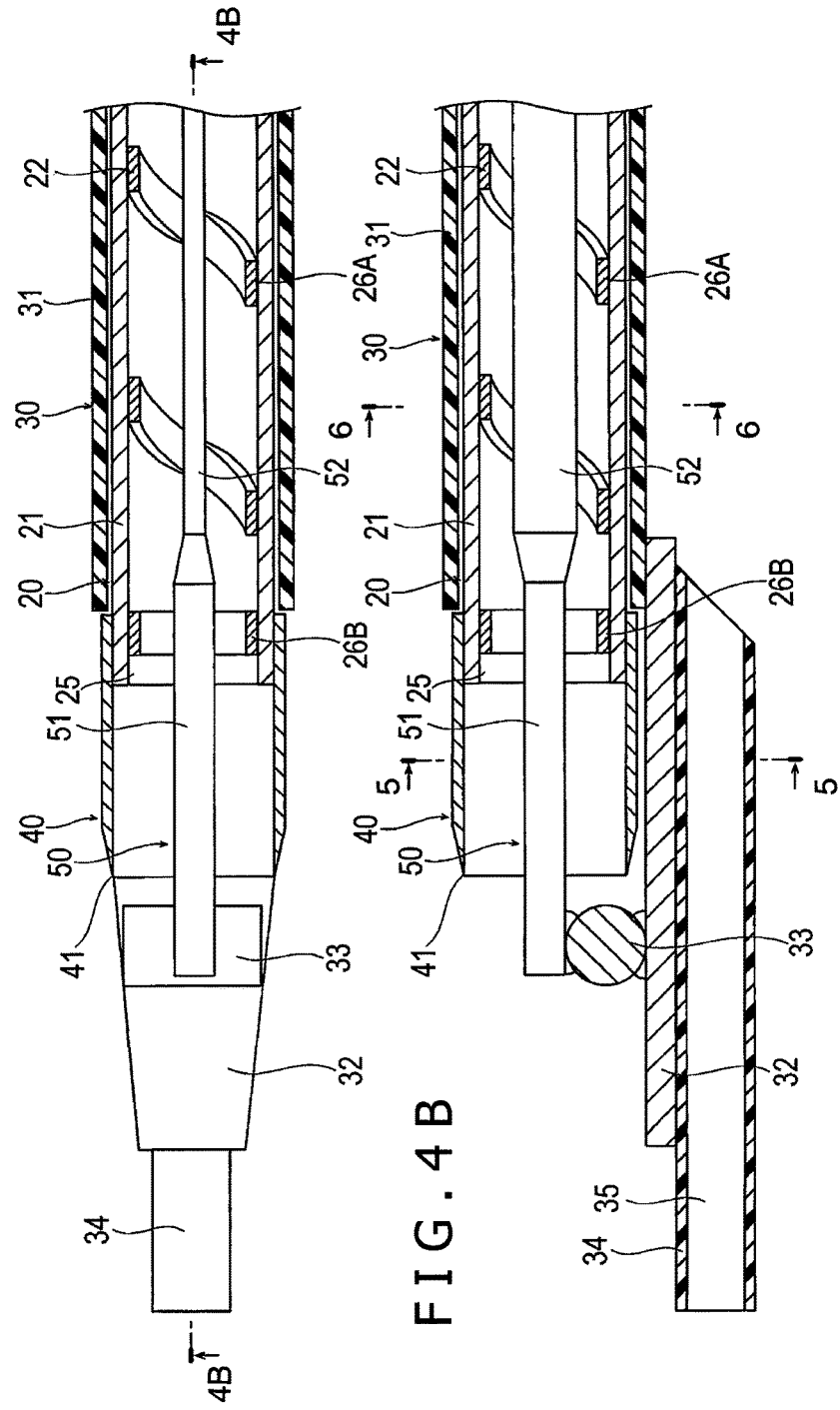
FIGS. 4A and 4B are diagrams illustrating a distal portion of a treatment device, FIG. 4A being a sectional view, and FIG. 4B being a sectional view taken along the section line 4B-4B of FIG. 4A.
Figure 5:
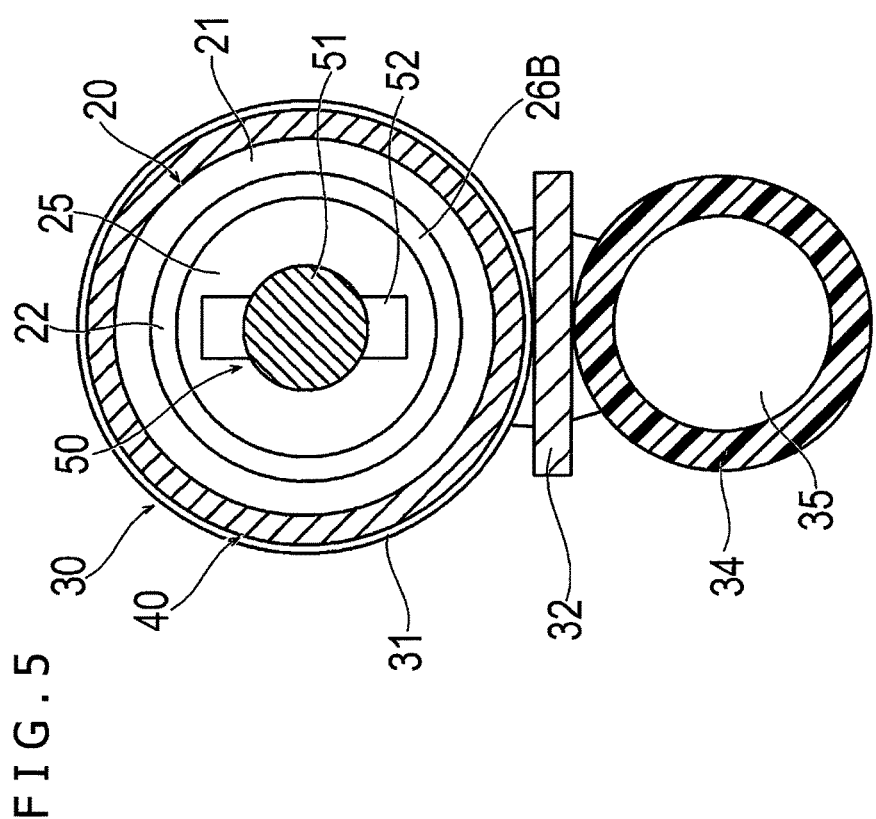
FIG. 5 is a sectional view taken along the section line 5-5 of FIG. 4B.

As illustrated in FIGS. 1 to 3, the medical device 10 includes: a driven shaft 20 that has a long length (elongated driven shaft) and is driven for rotation; an outer tube 30 that houses the driven shaft 20; a cutting unit 40 that cuts a thrombus; and a resistor 50 disposed within the driven shaft 20. The medical device 10 further includes: an operation unit 60 provided at a proximal side end portion of the outer tube 30; a rotation-driving unit 90 that rotates the driven shaft 20; a suction tubular body 70 interlocked to the driven shaft 20 within the operation unit 60; and a syringe 100 connected to the operation unit 60.

The driven shaft 20 is a part for transmitting a rotational force to the cutting unit 40 and conveying the object entering the lumen of the driven shaft 20 to the proximal side or in the proximal direction toward the proximal end. The driven shaft 20 includes an interior communicating with open proximal and distal ends of the driven shaft 20. As illustrated in FIGS. 2 to 7, the driven shaft 20 includes: a driven tube 21 possessing a long (elongated) tubular shape; a spiral-shaped conveying body 22 provided to an inner circumferential surface of the driven tube 21; and a connecting shaft 23 that connects the driven tube 21 and the rotation-driving unit 90 to each other.

The driven tube 21 penetrates the outer tube 30, and has the cutting unit 40 fixed to a distal portion thereof. A proximal portion of the driven tube 21 is located in a housing space 61 within the operation unit 60. The driven tube 21 is rotation-driven by the rotation-driving unit 90 via the connecting shaft 23. The driven tube 21 has a leading-out hole 24 in a side surface of the proximal portion thereof located in the housing space 61. The leading-out hole 24 communicates with the interior of the driven tube 24 and is spaced distally from the open proximal end of the driven tube as shown in FIG. 3. The driven tube 21 has, at a distal side end portion thereof, an entry portion 25 through which a thrombus enters. The lumen at the proximal side end portion of the driven tube 21 is closed. The connecting shaft 23 is fixed to the proximal side end portion of the driven tube 21. The leading-out hole 24 is an exit from which the thrombus entering the inside of the driven tube 21 from the entry portion 25 is discharged.

The driven tube 21 is flexible and has a property of being able to transmit rotational power acting from the proximal side to the distal side. The driven tube 21 includes, for example, a distal side driven tube 21A formed by arranging, spirally winding, and interlocking a plurality of wires, and a proximal side driven tube 21B, which is a tubular body interlocked to the proximal side of the distal side driven tube 21A (see FIG. 7). The distal side driven tube 21A has slits (gaps) penetrating from an inner circumferential surface to an outer circumferential surface between adjacent wires. A winding direction of spirals of the wires is desirably an opposite direction from a winding direction of spirals of the conveying body 22, but is not limited to this. When the winding direction of the spirals of the wires is the opposite direction from the winding direction of the spirals of the conveying body 22, strength is improved because the different spirals reinforce each other, and operability is improved because operation anisotropy is reduced. Note that the constitution or configuration of the driven tube is not particularly limited. For example, the driven tube may be a tubular body in which slits in a spiral shape are formed by laser processing or the like.

Examples of a suitably usable constituent material for the driven tube 21 include stainless steel, Ta, Ti, Pt, Au, W, polyolefin such as polyethylene, polypropylene, or the like, polyamide, polyester such as polyethylene terephthalate or the like, a fluorine-based polymer such as ethylene tetrafluoroethylene (ETFE) or the like, PEEK (polyetheretherketone), polyimide, or the like. In addition, the driven tube 21 may be formed of a plurality of materials, and a reinforcing member such as a wire or the like may be implanted or embedded in the driven tube 21.

The inside diameter of the driven tube 21, though suitably selectable, may be, for example, 0.5 to 3.0 mm. The outside diameter of the driven tube 21, though suitably selectable, may be, for example, 0.8 to 4.0 mm. The length in an axial direction of the driven tube 21, though suitably selectable, may be, for example, 150 to 2000 mm.

The connecting shaft 23 has a distal side end portion thereof fixed to the driven tube 21. The connecting shaft 23 has, on a proximal side thereof, an interlocking shaft 23A to be interlocked to the rotation-driving unit 90 to receive rotational power. A constituent material for the connecting shaft 23 is not particularly limited as long as the constituent material can transmit rotational power. A constituent material for the connecting shaft 23 is, for example, stainless steel. The rotation-driving unit 90 may be directly connected to the driven tube 21. In this case, the proximal side of the driven tube 21 has a notch. The rotation-driving unit 90 is interlocked to the notch. In this case, the lumen of the driven tube 21 which lumen is on a base end side of the leading-out hole 24 is sealed.

The conveying body 22 is a spiral part provided at the inner circumferential surface of the driven tube 21 and rotation-driven by the driven tube 21. When the conveying body 22 is rotated, the conveying body 22 makes a force directed to the proximal side (proximal end) act on a thrombus that has entered the lumen of the driven tube 21, and thus moves the thrombus in the proximal direction to the proximal side or proximal end. In addition, the lumen of the driven tube 21 has the role of a lumen for producing a suction force acting from the proximal side act on the distal side. The conveying body 22 includes: a first conveying body 26 disposed inside the distal portion of the driven tube 21; and a second conveying body 27 disposed more to the proximal side than the first conveying body 26 within the driven tube 21. The first conveying body 26 has a longer or greater spiral pitch distance than the second conveying body 27. The pitch distance refers to a moving distance in an axial direction when a spiral is wound 360 degrees in a circumferential direction. Stated differently, the pitch distance refers to the axial distance (parallel to the central axis) between axially adjacent windings or the axial distance between two points on the spiral that are 360 degrees apart in the circumferential direction. The first conveying body 26 having a longer pitch distance (greater pitch) than the second conveying body 27 has a longer conveying distance in one rotation, and thus conveys a larger amount of thrombus. Therefore, because the first conveying body 26 having a long pitch distance is disposed in the distal portion of the driven tube 21, the lumen on an entry side (distal side) that the thrombus enters can always be maintained in a state of not being clogged with any thrombus. The first conveying body 26 having such a long pitch distance also receives a large reaction force from the thrombus being conveyed, and thus needs a certain degree of strength. Therefore, in the present embodiment, the first conveying body 26 is manufactured by laser processing rather than of a coil formed by winding a wire. The first conveying body may be manufactured by winding a wire as long as the first conveying body can ensure adequate strength and can be rotated within the outer tube 30. Alternatively, the conveying body 22 may include: a second conveying body 27 disposed inside the distal portion of the driven tube 21; and a first conveying body 26 disposed more to the proximal side than the second conveying body 27 within the driven tube 21. Therefore, the second conveying body 27 having a shorter pitch distance than the first conveying body 26 is located on the distal side. This renders the distal portion of the driven shaft 20 flexible, and improves the ease with which the medical device 10 reaches the object to be cut.

The first conveying body 26 includes: a spiral portion 26A having a spiral shape; a distal side ring portion 26B located on the distal side of the spiral portion 26A; and a proximal side ring portion 26C located on the proximal side of the spiral portion 26A. The distal side ring portion 26B and the proximal side ring portion 26C are a tubular or annular body continuous over 360 degrees. The distal side ring portion 26B and the proximal side ring portion 26C fix the first conveying body 26 to the inner circumferential surface of the driven tube 21. The first conveying body 26 is fixed to the driven tube 21 by welding or bonding, for example. Alternatively, the first conveying body 26 may be fixed to the driven tube 21 by fitting (frictional force). Because the first conveying body 26 is fixed to the driven tube 21 by part of the first conveying body 26, an unfixed part of the first conveying body 26 (spiral portion 26A in the present embodiment) is flexibly deformable. Thus, the first conveying body 26 can be temporarily deformed by a force received from the thrombus being conveyed. Therefore damage to the first conveying body 26 can be suppressed. Positions at which the first conveying body 26 is fixed to the driven tube 21 and the number of fixed locations are not particularly limited. For example, the whole of an outer circumferential surface of the first conveying body 26 may be fixed to the driven tube 21. Alternatively, only one of the distal side and the proximal side of the first conveying body 26 may be fixed to the driven tube 21. The spiral portion 26A, the distal side ring portion 26B, and the proximal side ring portion 26C have an identical inside diameter and an identical outside diameter. The distal side ring portion 26B and the proximal side ring portion 26C provide a smooth inner circumferential surface over 360 degrees in end portions of the first conveying body 26. Therefore, the distal side ring portion 26B and the proximal side ring portion 26C are in smooth contact with but do not interfere with the resistor 50 located within and relatively rotated. It is thus possible to suppress damage to the distal side ring portion 26B and the proximal side ring portion 26C. The distal side ring portion 26B may not be provided. In this case, the spiral portion 26A having a spiral shape further extends spirally to the distal side. In this case, the vicinity of a distal side end portion of the spiral portion 26A having a spiral shape is joined to the driven tube 21 by welding or the like. This can reduce a volume occupied by the first conveying body 26 and thus enlarge the space of the lumen of the driven shaft 20. Therefore, many objects can be guided and conveyed to the lumen of the driven shaft 20 more smoothly. In the case where the spiral portion 26A having a spiral shape constitutes the distal side end portion of the first conveying body 26, the distal side end portion of the spiral portion 26A is disposed in the vicinity of the position of the distal side end portion of the cutting unit 40. Thus, the object cut by the cutting unit 40 can be continuously guided to the spiral portion 26A. Therefore, the thrombus T is rather easily sent through the lumen of the driven shaft 20 to the proximal side, and the lumen is not easily clogged.

The second conveying body 27 is a spiral member having a shorter pitch distance than the first conveying body 26. The second conveying body 27 is, for example, a coil. Part (for example, a distal side end portion and a proximal side end portion) of the second conveying body 27 is fixed to the inner circumferential surface of the driven tube 21. The second conveying body 27 is fixed to the driven tube 21 by welding or bonding, for example. Alternatively, the second conveying body 27 may be fixed to the driven tube 21 by fitting (frictional force). Because the second conveying body 27 is fixed to the driven tube 21 by part of the second conveying body 27, an unfixed part of the second conveying body 27 is flexibly deformable. Thus, the second conveying body 27 can be temporarily deformed by a force received from the thrombus being conveyed. Therefore damage to the second conveying body 27 can be suppressed. Positions at which the second conveying body 27 is fixed to the driven tube 21 and the number of fixed locations are not particularly limited. For example, the whole of an outer circumferential surface of the second conveying body 27 may be fixed to the driven tube 21. Alternatively, only one of the distal side and the proximal side of the second conveying body 27 may be fixed to the driven tube 21. The second conveying body 27, which is a coil, is manufactured easily even when having a long length, and can be reduced in cost. In addition, the second conveying body 27, which is a coil, is rather easily inserted into and disposed within the driven tube 21. The shape of a cross section of the second conveying body 27 which cross section is perpendicular to a central axis of the second conveying body 27 is not particularly limited, but is, for example, a square, a rectangle, a parallelogram, a trapezoid, a circle, an oval, or the like.

A constituent material for the first conveying body 26 and the second conveying body 27 desirably has a certain degree of strength so as to be able to convey the object. Examples of suitably usable constituent material for the first conveying body 26 and the second conveying body 27 include a shape memory alloy to which a shape memory effect or superelasticity is imparted by heat treatment, stainless steel, Ta, Ti, Pt, Au, W, polyolefin such as polyethylene, polypropylene, or the like, polyamide, polyester such as polyethylene terephthalate or the like, a fluorine-based polymer such as ETFE or the like, PEEK, polyimide, or the like. Desirably used as the shape memory alloy is a Ni—Ti based alloy, a Cu—Al—Ni based alloy, a Cu—Zn—Al based alloy, combinations thereof, or the like. When the first conveying body 26 and the second conveying body 27 are manufactured of a shape memory alloy, the first conveying body 26 and the second conveying body 27 can excellently return to the original shape after being deformed temporarily by the reaction force received from the thrombus. It is therefore possible to maintain the functions of the first conveying body 26 and the second conveying body 27 while suppressing damage to the first conveying body 26 and the second conveying body 27. The first conveying body 26 and the second conveying body 27 may be formed of respective different constituent materials.

An angle of inclination $\alpha$ of the spiral of the first conveying body 26 with respect to a central axis of the first conveying body 26, though suitably settable, is, for example, 10 to 75 degrees, preferably 15 to 40 degrees, more preferably 25 to 35 degrees. An angle of inclination $\beta$ (helix angle) of the spiral of the second conveying body 27 with respect to the central axis of the second conveying body 27 is larger than the angle of inclination $\alpha$ of the spiral of the first conveying body 26, and is, for example, 25 to 80 degrees, preferably 30 to 60 degrees, more preferably 35 to 45 degrees. In a case of a large angle of inclination, the pitch distance is shortened, and therefore the conveying distance in one rotation is shortened. However, it is possible to reduce a force necessary for conveyance, and thus suppress damage and improve safety. In a case of a small angle of inclination, the pitch distance is lengthened, and therefore the conveying distance in one rotation is lengthened. However, a force necessary for conveyance is increased, and it is thus necessary to enhance rigidity or flexibility to suppress damage.

The inside diameter of the first conveying body 26 and the second conveying body 27, though suitably selectable, may be, for example, 0.4 to 2.8 mm. The outside diameter of the first conveying body 26 and the second conveying body 27 desirably has a predetermined clearance with respect to the inner circumferential surface of the driven tube 21 so that the first conveying body 26 and the second conveying body 27 can be inserted into the driven tube 21 and be in contact with the inner wall surface of the driven tube 21. The outside diameter of the first conveying body 26 and the second conveying body 27 is, for example, 0.49 to 2.99 mm. The inside diameter of the first conveying body 26 may be different from the inside diameter of the second conveying body 27. In addition, the outside diameter of the first conveying body 26 may be different from the outside diameter of the second conveying body 27.

The length in the axial direction of the first conveying body 26, though suitably selectable, may be, for example, 5 to 300 mm. The length in the axial direction of the second conveying body 27, though suitably selectable, may be, for example, 301 to 1995 mm. The conveying body 22 may be only the first conveying body 26. In that case, the length in the axial direction of the first conveying body 26 may be 1 to 2000 mm.

The outer tube 30 includes: an outer sheath 31 that rotatably houses the driven shaft 20; an extension 32 fixed to an outer circumferential surface of a distal portion of the outer sheath 31; a fixing portion 33 that fixes the extension 32 and the resistor 50; and a distal end tube 34 fixed to the extension 32.

The outer sheath 31 is a tubular body. The outer sheath 31 has a proximal side end portion thereof fixed to the operation unit 60. A distal side end portion of the outer sheath 31 is located on the proximal side of the cutting unit 40. The cross-sectional area of a clearance between the outer sheath 31 and the driven tube 21 is desirably sufficiently smaller than the cross-sectional area of the inside of the suction tubular body 70. It is thereby possible to prevent a suction force acting on the inside of the driven tube 21 from the suction tubular body 70 from diffusing into a space between the outer sheath 31 and the driven tube 21 through the slits between the wires of the driven tube 21.

The extension 32 is fixed to part of the outer circumferential surface of the distal portion of the outer sheath 31, and extends more to the distal side than the outer sheath 31. That is, the extension 32 extends distally beyond the distal end of the outer sheath 31. The extension 32 is a member for fixing the resistor 50 and the distal end tube 34 to the outer sheath 31. The extension 32 is provided only to part in the circumferential direction of the outer circumferential surface of the outer sheath 31 so as not to hinder the cutting of the thrombus by the cutting unit 40. In other words, the extension 32 is of limited circumferential extent in that the extension 32 has a circumferential extent less than 360°. The extension 32 is, for example, a plate material or a plate. However, the shape of the extension 32 is not limited. The extension 32 may be, for example, a wire.

The fixing portion 33 is a member for fixing a part on the distal side of the extension 32 and the resistor 50. That is, the fixing portion 33 fixes a distal end portion of the extension 32 and the resistor 50. The fixing portion 33 is located on the extension 32 and is positioned distally of the cutting unit 40. The fixing portion 33 plays a role of bridging a distance between the extension 32 and the resistor 50 that are spaced apart from each other. Hence, the fixing portion 33 has such a size as to be able to dispose the resistor 50 at an appropriate position with respect to the extension 32. The fixing portion 33 is, for example, a wire. However, the shape of the fixing portion 33 is not limited. The fixing portion 33 may, for example, be a part integral with the extension 32 and the resistor 50.

The distal end tube 34 is fixed to the extension 32. The distal end tube 34 internally has a guide wire lumen 35 into which a guide wire can be inserted.

A constituent material for the outer sheath 31 is not particularly limited. However, examples of suitably usable constituent materials for the outer sheath 31 include polyolefin such as polyethylene, polypropylene, or the like, polyamide, polyester such as polyethylene terephthalate or the like, or various kinds of elastomers, a fluorine-based polymer such as ETFE or the like, PEEK, polyimide, or the like. In addition, the outer sheath 31 may be formed of a plurality of materials, and a reinforcing member such as a wire or the like may be implanted or embedded in the outer sheath 31.

The inside diameter of the outer sheath 31, though suitably selectable, may be, for example, 0.9 to 4.1 mm, more preferably 1.2 to 1.9 mm. The outside diameter of the outer sheath 31, though suitably selectable, may be, for example, 1.0 to 4.5 mm, more preferably 1.3 to 2.0 mm.

A constituent material for the extension 32 and the fixing portion 33 desirably has a certain degree of strength. Examples of suitably usable constituent material for the extension 32 and the fixing portion 33 include a shape memory alloy to which a shape memory effect or superelasticity is imparted by heat treatment, stainless steel, Ta, Ti, Pt, Au, W, polyolefin such as polyethylene, polypropylene, or the like, polyamide, polyester such as polyethylene terephthalate or the like, a fluorine-based polymer such as ETFE or the like, PEEK, polyimide, or the like. Desirably used as the shape memory alloy is a Ni—Ti based alloy, a Cu—Al—Ni based alloy, a Cu—Zn—Al based alloy, combinations thereof, or the like.

The length in the axial direction of the extension 32, though suitably selectable, may be, for example, 0.3 to 50 mm, more preferably 1 to 5 mm. The thickness of the extension 32 (length along the radial direction of the outer sheath 31), though suitably selectable, may be, for example, 0.05 to 1 mm. The width of the extension 32 (length along the circumferential direction of the outer sheath 31), though suitably selectable, may be, for example, 0.1 to 2 mm.

A constituent material for the distal end tube 34 is not particularly limited. However, examples of a suitably usable constituent material for the distal end tube 34 include polyolefin such as polyethylene, polypropylene, an ethylene-propylene copolymer, an ethylene-vinyl acetate copolymer, or the like, polyvinyl chloride, polystyrene, polyamide, polyimide, combinations thereof, or the like.

The inside diameter of the distal end tube 34, though suitably selectable, may be, for example, 0.3 to 1.0 mm. The outside diameter of the distal end tube 34, though suitably selectable, may be, for example, 0.4 to 1.4 mm. The length in the axial direction of the distal end tube 34, though suitably selectable, may be, for example, 5 to 100 mm.

The cutting unit 40 is a part for cutting the thrombus. The cutting unit 40 is fixed to an outer circumferential surface of the distal portion of the driven tube 21. The cutting unit 40 is a cylinder projecting more to the distal side than the driven tube 21. That is, the cutting unit 40 projects distally beyond the distal end of the driven tube 21. The distal side end portion of the cutting unit 40 has a ring-shaped sharp edge 41, which is formed by reducing the outside diameter of the distal side end portion of the cutting unit 40 toward the distal side until the outside diameter coincides with the inside diameter of the distal side end portion of the cutting unit 40.

A constituent material for the cutting unit 40 desirably has such a degree of strength as to be able to cut the thrombus. Examples of suitably usable constituent material for the cutting unit 40 includes, for example, stainless steel, Ta, Ti, Pt, Au, W, a shape memory alloy, or the like. A constituent material for the cutting unit 40 may be a resin such as PEEK or another engineering plastic or the like. The surface of the cutting unit 40 may be subjected to coating treatment.

The inside diameter of the cutting unit 40 desirably substantially coincides with the outside diameter of the driven tube 21 that the cutting unit 40 is in contact with. The inside diameter of the cutting unit 40 may be, for example, 0.8 to 40 mm. The outside diameter of the cutting unit 40 desirably substantially coincides with the outside diameter of the outer sheath 31. The outside diameter of the cutting unit 40 may be, for example, 1.0 to 4.5 mm. The length in the axial direction of the cutting unit 40, though suitably selectable, may be, for example, 0.5 to 4.0 mm.

Figure 6:
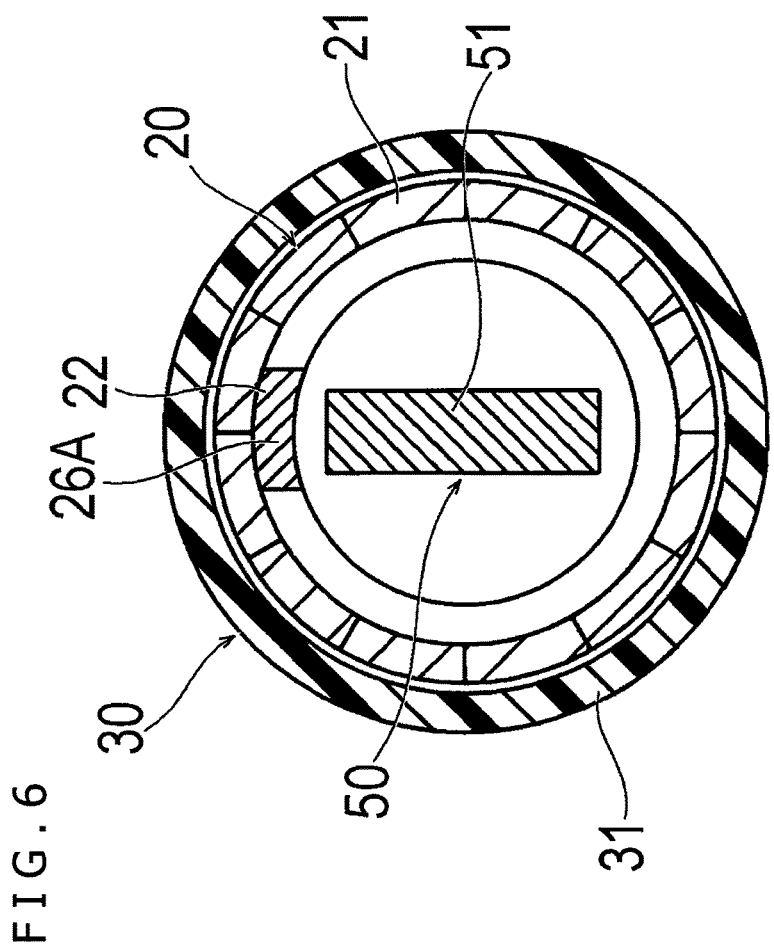
FIG. 6 is a sectional view taken along the section line 6-6 of FIG. 4B.
Figure 7:
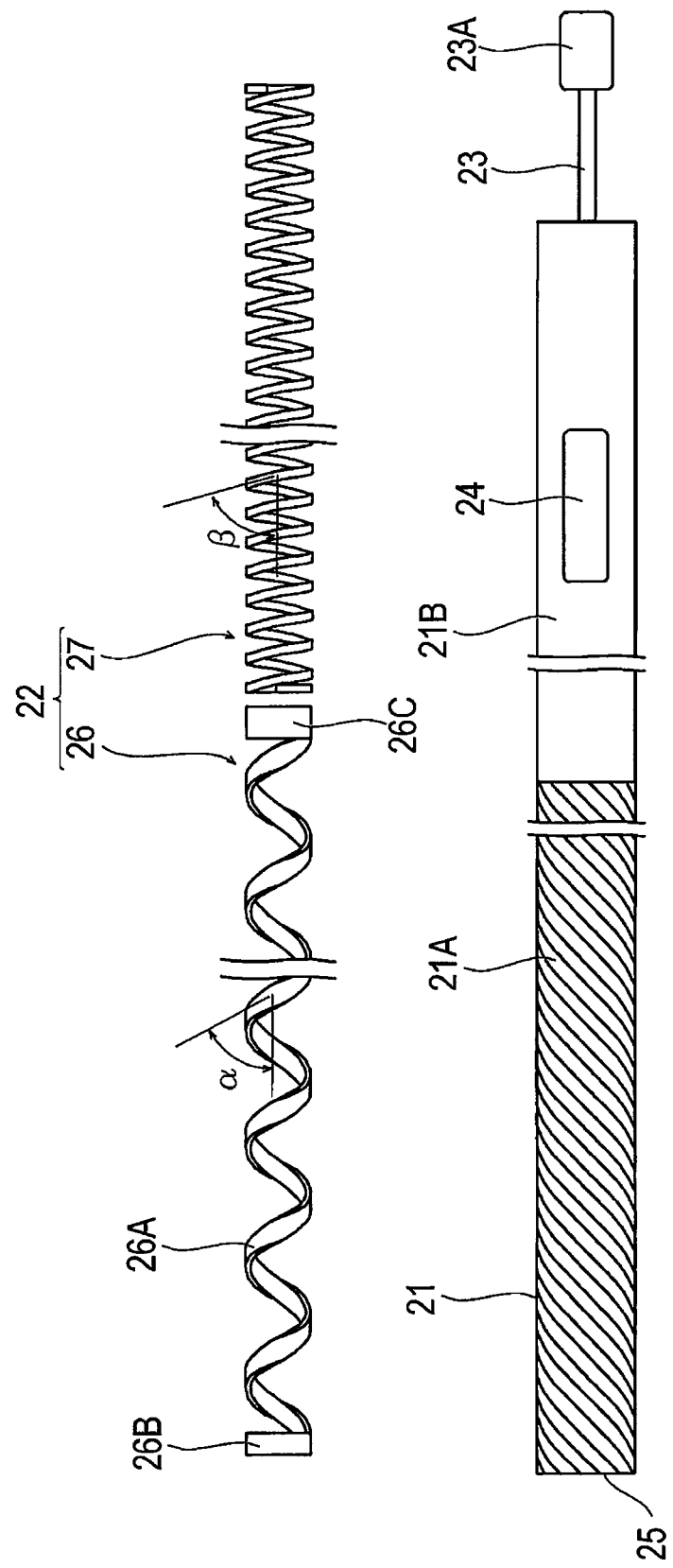
FIG. 7 is a plan view illustrating a driven shaft in a disassembled state.

The resistor 50 is elongated part disposed in the lumen of the driven shaft 20 and rotatable relative to the driven shaft 20. The resistor 50 prevents the thrombus that has entered the inside of the driven shaft 20 from rotating together with the driven shaft 20. The shape of a cross section of at least part of the resistor 50, which cross section is perpendicular to a central axis of the resistor 50, is a non-perfect circle or is non-circular. FIG. 6 shows an example of a non-circular cross-section (i.e., rectangular cross-section. The resistor 50 includes: a first resistor 51 located on the distal side or distal end of the resistor 50; and a second resistor 52 located on the proximal side or proximal end of the resistor 50. The first resistor 51 and the second resistor 52 have different cross-sectional shapes perpendicular to the central axis. The shape of the cross section of the first resistor 51 which cross section is perpendicular to the central axis is a perfect circle. The shape of the cross section of the second resistor 52 which cross section is perpendicular to the central axis is substantially rectangular. Such a resistor 50 can be manufactured rather easily by leaving part of a wire having a perfect circle as a sectional shape as it is as the first resistor 51 and forming the second resistor 52 in the shape of a flat plate (rectangle) by sandwiching and crushing another part of the wire using a die. A flat plate refers to a shape having a sectional shape relatively long in one of two directions orthogonal to each other and generally having two surfaces facing in opposite directions. The first resistor 51 and the second resistor 52 may be manufactured by joining different members to each other. A distal side end portion of the resistor 50 is fixed to the fixing portion 33 at a position more to the distal side than the cutting unit 40. That is, the location at which the resistor 50 is fixed to the fixing portion 33 is distal of the cutting unit 40. The first resistor 51, which has a perfect circle as the shape of a cross section of a distal portion of the resistor 50 which cross section is perpendicular to the central axis, has an exterior surface that offers low resistance or that presents little of an impediment to thrombus. Thus, the thrombus rather easily enters the inside of the cutting unit 40 and the driven shaft 20. An interlock portion (connecting portion) between the first resistor 51 and the second resistor 52 is located within the conveying body 22. Therefore, the thrombus can be guided to the inside of the conveying body 22 along the first resistor 51 whose exterior surface exhibits a low resistance. An end portion on the proximal side of the second resistor 52 is located more to the proximal side than the conveying body 22. That is, the proximal end portion of the second resistors projects proximally beyond the proximal end of the conveying body 22. The second resistor 52 thereby prevents the thrombus from rotating together with the driven shaft 20 until the thrombus is positioned on the proximal side of the conveying body 22. A high conveying force can therefore be maintained. The proximal end portion of the resistor 50 is located within the suction tubular body 70, but may not be located within the suction tubular body 70. The proximal end portion of the resistor 50 may be located on the proximal side of the first conveying body 26 and on the distal side of the proximal end portion of the second conveying body 27. It is thereby possible to maintain a high conveying force in the position of the first conveying body 26 on the distal end side where a high conveying force is desired.

Because the shape of the cross section of the second resistor 52, which cross section is perpendicular to the central axis and is a non-perfect circle or a non-circle, a second space is always present between the outer surface of the second resistor 52 and an inner circumferential surface of the driven shaft 20 that rotates relative to the second resistor 52 (resistor 50). In addition, a first space is present between the outer surface of the first resistor 51 and the inner circumferential surface of the driven shaft 20 and between the outer surface of the first resistor 51 and an inner circumferential surface of the cutting unit 40. The space between the resistor 50 and the driven shaft 20 and the space between the resistor 50 and the cutting unit 40 function effectively to make a suction force act from the proximal side.

The first resistor 51 has the same cross-sectional shape perpendicular to the central axis over its entire extent in the axial direction. The first resistor 51 therefore has a smooth surface along the axial direction. Thus, the thrombus or the like can slide smoothly along the first resistor 51. The second resistor 52 has the same cross-sectional shape perpendicular to the central axis over its entire extent in the axial direction. The second resistor 52 therefore has a smooth surface along the axial direction. Thus, the thrombus or the like can slide smoothly along the second resistor 52.

A constituent material for the resistor 50 desirably has such a degree of strength as to be able to suppress the rotation of the thrombus. Examples of suitably usable constituent material for the resistor 50 include stainless steel, Ta, Ti, Pt, Au, W, a shape memory alloy such as Nitinol (registered trademark), or the like.

The operation unit 60 is a part held and operated by an operator. As illustrated in FIG. 3, the operation unit 60 includes: a casing 62 internally having the housing space 61; a first seal portion 63 in contact with an outer circumferential surface of the driven shaft 20; and a second seal portion 64 in contact with an outer circumferential surface of the connecting shaft 23.

The casing 62 includes: a distal side through hole 65 that the driven tube 21 penetrates; a proximal side through hole 66 that the connecting shaft 23 penetrates; and a suction hole 67 to which the syringe 100 can be interlocked. The distal side through hole 65, the proximal side through hole 66, and the suction hole 67 communicate with the housing space 61. The distal side through hole 65 is penetrated by the driven tube 21, and is interlocked with a proximal portion of the outer sheath 31. In addition, the first seal portion 63 in contact with an outer circumferential surface of the driven tube 21 is disposed in the distal side through hole 65. The first seal portion 63 seals off a space between the driven tube 21 and the outer sheath 31 from the housing space 61 while allowing the rotation of the driven tube 21. The first seal portion 63 functions to maintain the negative pressure of the housing space 61. The first seal portion 63 also prevents a negative pressure between the driven tube 21 and the outer sheath 31 from escaping into the housing space 61. The proximal side through hole 66 is penetrated by the connecting shaft 23, and has the second seal portion 64 disposed therein, the second seal portion 64 being in contact with the outer circumferential surface of the connecting shaft 23. The second seal portion 64 seals off the housing space 61 from the outside while allowing the rotation of the connecting shaft 23. The second seal portion 64 functions to maintain the negative pressure of the housing space 61. The suction hole 67 allows the syringe 100 to be interlocked to the suction hole 67. Suction by the syringe 100 interlocked to the suction hole 67 can cause a negative pressure in the housing space 61 communicating with the suction hole 67. The first seal portion 63 and the second seal portion 64 are, for example, an O-ring.

The suction tubular body 70 is a tubular body for guiding the negative pressure of the housing space 61 to a predetermined position within the driven tube 21. A distal side opening portion 72 of the suction tubular body 70 is located on the proximal side of the second conveying body 27 within the driven tube 21. An outer circumferential surface of a distal side end portion of the suction tubular body 70 is in close liquid-tight contact with the inner circumferential surface of the driven tube 21. Therefore, even when the driven tube 21 housing the suction tubular body 70 is formed of wires and has a plurality of slits (gaps), the negative pressure can be made to act effectively up to the distal side end portion of the suction tubular body 70. A part on the proximal side of the suction tubular body 70, which part is provided with a proximal side opening portion 73, is led out outward from the leading-out hole 24 of the driven tube 21. The suction tubular body 70 includes a whirling portion 71 located on the outside of the driven tube 21. The whirling portion 71 is inclined so as to extend away from the driven tube 21 toward the proximal side from the leading-out hole 24. That is, the whirling portion 71 formed by the proximal portion of the suction tubular body 70 extends in a direction in which the whirling portion 71 separates from the driven shaft in the radially outward direction of the driven shaft so that the axis of the whirling portion is at an oblique angle relative to both the central axis of the driven shaft and the central axis of the portion of the suction tubular body 70 positioned inside and surrounded by the driven shaft. The whirling portion 71 thus extends in a direction in which the whirling portion 71 is angled relative to the driven shaft so that the whirling portion 71 of the suction tubular body separates at progressively greater distances from the driven shaft toward the open proximal end of the suction tubular body. Hence, the proximal side opening portion 73 of the suction tubular body 70 is separated from the external surface of the driven tube 21. The whirling portion 71 of the suction tubular body 70 whirls when the driven tube 21 is rotated. When the whirling portion 71 whirls, a centrifugal force acts on matter within the whirling portion 71, and the matter moves toward the proximal side opening portion 73. A negative pressure therefore occurs within the suction tubular body 70. Hence, even when there is no acting suction force produced by the syringe 100, the rotation of the driven tube 21 can generate a negative pressure within the driven tube 21 communicating with the suction tubular body 70. In addition, because the whirling portion 71 is inclined with respect to the driven tube 21, a longer whirling portion 71 exists, as compared to the case where the whirling portion 71 is at a right angle to the driven tube 21. The longer whirling portion 71 can thus be disposed within the housing space 61 in which a radius of gyration is limited. Therefore, the volume of the matter on which the centrifugal force acts when the whirling portion 71 whirls is increased, so that the negative pressure can be generated excellently. Further, because the whirling portion 71 is inclined with respect to the driven tube 21, the matter flowing through the suction tubular body 70 flows smoothly as compared with the case where the whirling portion 71 is at a right angle to the driven tube 21. The negative pressure can consequently be generated excellently.

A constituent material for the suction tubular body 70 is not particularly limited. However, examples of suitably usable material for the suction tubular body 70 include, for example, silicone resin, various elastomers, polyolefin such as polyethylene, polypropylene, an ethylene-propylene copolymer, an ethylene-vinyl acetate copolymer, or the like, polyvinyl chloride, polystyrene, polyamide, polyimide, combinations thereof, or the like.

The outside diameter of the suction tubular body 70, though suitably selectable, may, for example, to mm. The inside diameter of the suction tubular body 70, though suitably selectable, may be, for example, to mm. The length of the whirling portion 71, though suitably selectable, may be for example, to mm. The angle of inclination of the whirling portion 71 with respect to the driven tube 21, though suitably selectable, may 0 to 90 degrees, preferably to degrees, more preferably to degrees.

As illustrated in FIG. 1, the rotation-driving unit 90 is a part that includes a driving source 91 such as a motor or the like and which rotates the driven shaft 20. The rotation-driving unit 90 includes a rotatable rotating shaft 92 to which the connecting shaft 23 is connected. While the rotation-driving unit 90 in the present embodiment is an external device that can be interlocked to and detached from the operation unit 60, the rotation-driving unit 90 may be fixed to the operation unit 60. The rotation-driving unit 90 further includes a switch, a battery, and the like, which are not illustrated.

A method of using the medical device 10 according to the first embodiment will next be described by taking as an example a case where a thrombus, a calcified lesion, or the like within a blood vessel is destroyed and sucked or extracted.

Figure 8:
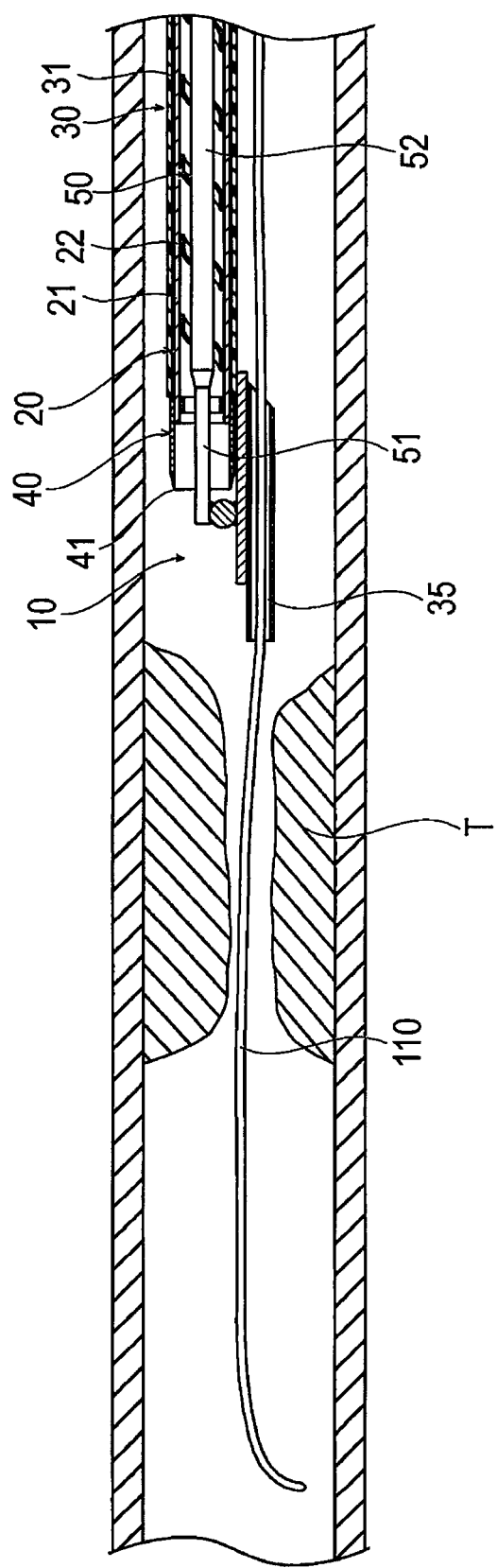
FIG. 8 is a sectional view illustrating a state in which the medical device is inserted in a blood vessel.

First, the medical device 10 is prepared so that the rotation-driving unit 90 is interlocked to the operation unit 60 and the connecting shaft 23 is interlocked to the rotating shaft 92 (see FIG. 1). The medical device 10 is in a state in which the driven shaft 20 can be rotated by operating the rotation-driving unit 90. Next, a proximal side end portion of a guide wire 110 (see FIG. 8) is inserted into the guide wire lumen 35 of the medical device 10. Thereafter, with the guide wire 110 as a guide, the medical device 10 is moved or advanced to reach the distal side of the thrombus T.

Figure 9:
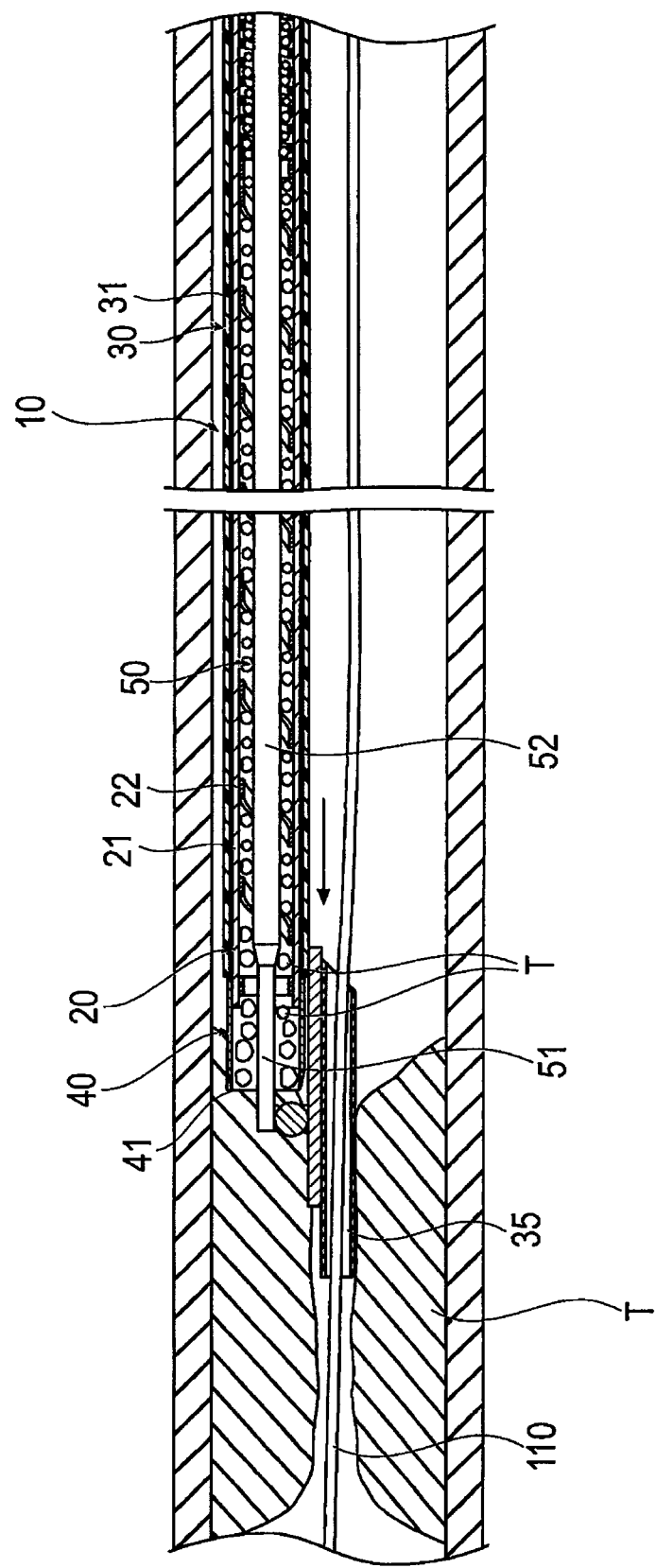
FIG. 9 is a sectional view illustrating a state in which a thrombus is removed by the medical device within the blood vessel.
Figure 10:
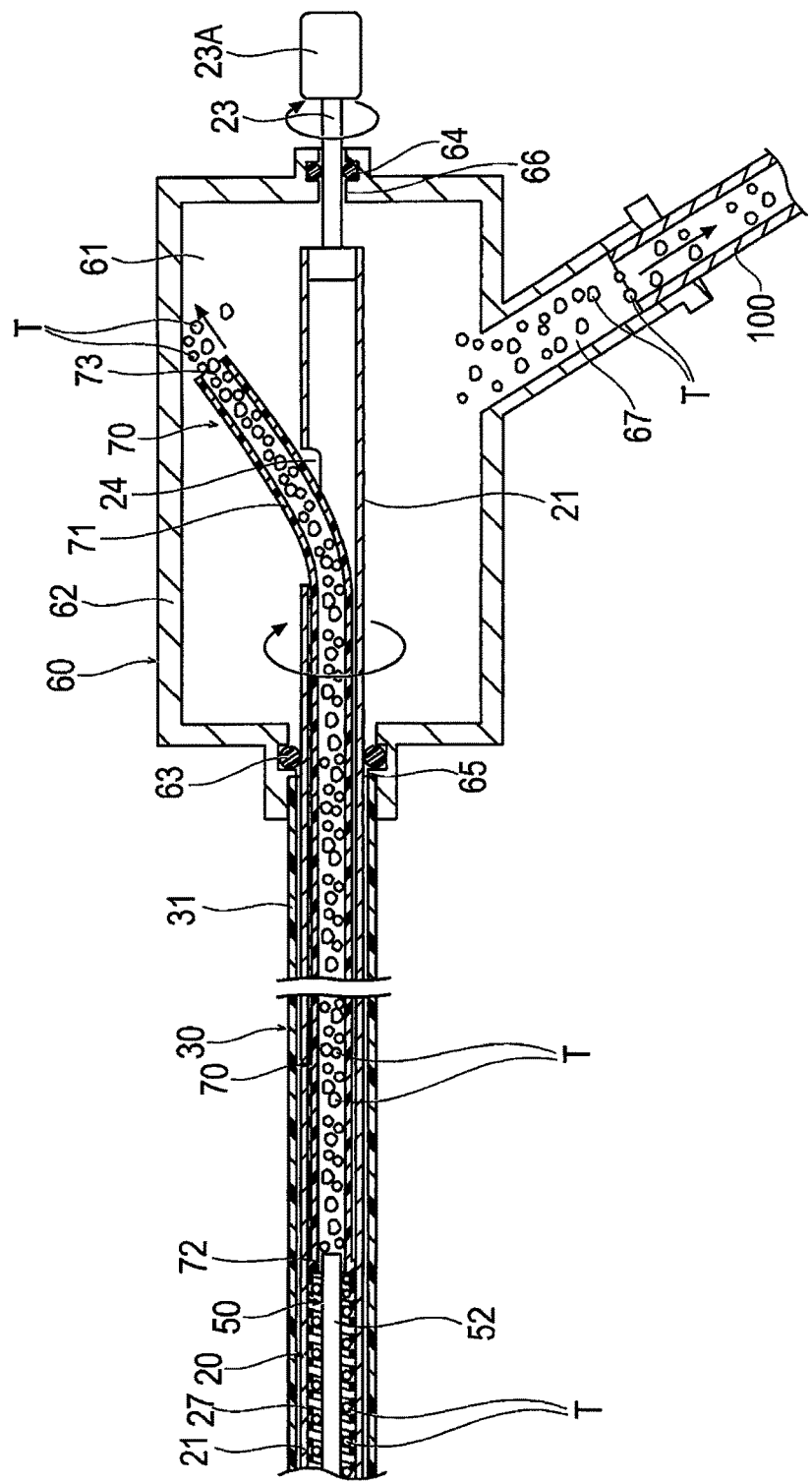
FIG. 10 is a sectional view illustrating the proximal portion of the medical device when the medical device is removing the thrombus within the blood vessel.

Next, the rotation-driving unit 90 is operated to rotate the driven shaft 20. The driven shaft 20 is thereafter moved to the distal side or in the distal direction. Thereby, as illustrated in FIGS. 9 and 10, the edge 41 of the cutting unit 40 comes into contact with the thrombus T, and the rotating edge 41 cuts the thrombus T. The cut thrombus T enters the inside of the driven tube 21 via the lumen of the tubular cutting unit 40. At this time, the first resistor 51 in which the shape of the cross section perpendicular to the central axis is a perfect circle is located within the cutting unit 40. Therefore, the thrombus T is rather smoothly guided to the driven tube 21 along the external surface of the first resistor 51 which external surface has a low resistance. Pushing in the medical device 10 can make it easier for the cut thrombus T to enter the inside of the driven tube 21 via the lumen of the tubular cutting unit 40.

The thrombus T guided into the driven tube 21 comes into contact with the first conveying body 26 that is rotating. The thrombus T thus receives a force acting in a proximal direction and a force acting in a rotational direction from the first conveying body 26. At this time, the second resistor 52 that penetrates the inside of the first conveying body 26 and does not rotate prevents the thrombus T from rotating together with the first conveying body 26. Therefore, the thrombus T efficiently moves linearly to the proximal side along the second resistor 52 due to the forces received from the rotating first conveying body 26 and a reaction force received from the second resistor 52. In addition, the first conveying body 26 has a longer pitch distance than the second conveying body 27, and thus conveys (axially moves) a larger amount in one rotation. Therefore, the lumens on the entry side of the cutting unit 40 and the driven shaft 20 (the thrombus T enter the lumens on the entry side) can be maintained in a state of not being clogged with the thrombus T at all times.

Further, the whirling portion 71 of the suction tubular body 70 whirls as the driven tube 21 rotates. Thereby, a centrifugal force acts on the matter within the whirling portion 71, and the matter within the whirling portion 71 moves toward the proximal side opening portion 73. A negative pressure therefore occurs within the suction tubular body 70. At this time, because the whirling portion 71 is inclined, the volume of the matter on which the centrifugal force acts when the whirling portion 71 whirls is increased. The negative pressure can therefore be generated excellently. Further, because the whirling portion 71 is inclined, the matter flowing through the suction tubular body 70 flows smoothly. The negative pressure can therefore be generated excellently. Further, when a plunger of the syringe 100 interlocked to the suction hole 67 is pulled, the housing space 61 in the operation unit 60 develops a negative pressure, and the inside of the suction tubular body 70 develops a negative pressure via the proximal side opening portion 73 of the suction tubular body 70. While the syringe 100 can be used as a source of the negative pressure, it is also possible to make a connection to a suction pump or the like.

When the inside of the suction tubular body 70 develops a negative pressure, the inside of the driven tube 21 communicating with the suction tubular body 70 also develops a negative pressure. At this time, the suction tubular body 70 is disposed within the proximal portion of the driven tube 21. The negative pressure can therefore be prevented from escaping from the slits as gaps between the wires of the driven tube 21. In in a region more to the distal side than the suction tubular body 70, the thrombus can be conveyed by the conveying body 22, and thus little or no problem is presented even when the negative pressure escapes slightly without the suction tubular body 70. The negative pressure can therefore be made to act excellently in a range where the conveying body 22 is provided in the driven tube 21. When the negative pressure acts on the inside of the driven tube 21, the thrombus T within the driven tube 21 moves to the proximal side or in the proximal direction. At this time, the rotating driven shaft 20 is located on the outside of a space as a conveyance path. In addition, because the resistor 50 located inside the rotating conveying body 22 has a non-perfect circle or non-circle (e.g., rectangle) as the shape of a cross section perpendicular to the central axis, a space is provided between an inner circumferential surface of the conveying body 22 and the resistor 50. A suction force within the driven tube 21 which suction force is generated by the negative pressure can therefore act on the thrombus T effectively. Thus, the thrombus T is moved linearly and conveyed effectively toward the proximal side or in the proximal direction by both the force of the first conveying body 26 and the suction force. The suction by the syringe 100 may be performed or may not be performed. In addition, because the first conveying body 26 is partly fixed to the driven tube 21 and is deformable, the first conveying body 26 can be deformed even when the thrombus T is relatively large, for example. Therefore, damage to the first conveying body 26 is suppressed, and a relatively high degree of safety is achieved. In addition, when the first conveying body 26 is formed of an elastically deformable material such as a shape memory alloy or the like, the first conveying body 26 can return to the original shape after being deformed. The performance of the first conveying body 26 can therefore be maintained.

The thrombus T, after moving to a position proximal of the first conveying body 26 reaches a position where the second conveying body 27 is disposed within the driven tube 21. The thrombus T thus receives a force acting in the proximal direction and a force acting in the rotational direction from the second conveying body 27. At this time, the second resistor 52 that penetrates the inside of the second conveying body 27 and does not rotate prevents the thrombus T from rotating together with the second conveying body 27. Therefore, the thrombus T efficiently moves linearly to the proximal side or in the proximal direction along the second resistor 52 due to the forces received from the rotating second conveying body 27 and a reaction force received from the second resistor 52.

In addition, the thrombus T reaching the position where the second conveying body 27 is disposed within the driven tube 21 receives the suction force from the suction tubular body 70 as in the case where the thrombus T is in a position where the first conveying body 26 is disposed. Thus, the thrombus T is moved linearly and conveyed effectively toward the proximal side or in the proximal direction by both the force of the second conveying body 27 and the suction force. The suction by the syringe 100 may be performed or may not be performed. In addition, because the second conveying body 27 is partly fixed to the driven tube 21 and is deformable, the second conveying body 27 can be deformed even when the thrombus T is relatively large, for example. Therefore, damage to the second conveying body 27 is suppressed, and a rather high degree of safety is achieved. In addition, when the second conveying body 27 is formed of an elastically deformable material such as a shape memory alloy or the like, the second conveying body 27 can return to the original shape after being deformed. The performance of the second conveying body 27 can therefore be maintained. Further, because the resistor 50 is located more to the proximal side than the first conveying body 26 and the second conveying body 27, conveyance by the first conveying body 26 and the second conveying body 27 is performed excellently.

The thrombus T that has reached a position proximal to the proximal end of the second conveying body 27 is sucked into the suction tubular body 70, and moves through the inside of the suction tubular body 70 to the proximal side. The thrombus T within the suction tubular body 70 thereafter reaches the inside of the housing space 61 from the proximal side opening portion 73. The thrombus T that has reached the inside of the housing space 61 is discharged into the syringe 100 via the suction hole 67. The thrombus T may be retained within the housing space 61 without being discharged into the syringe 100.

In addition, because the cross-sectional area of a gap between the outer sheath 31 and the driven tube 21 is sufficiently smaller than the cross-sectional area of the inside of the suction tubular body 70, the suction force acting on the inside of the driven tube 21 from the suction tubular body 70 can be prevented from escaping into the space between the outer sheath 31 and the driven tube 21.

In addition, when the syringe 100 generates a negative pressure in the housing space 61, the negative pressure can be made to act on the inside of the driven tube 21 effectively because the housing space 61 is sealed by the first seal portion 63 and the second seal portion 64.

Then, the thrombus T is cut by moving the cutting unit 40 while making the cutting unit 40 reciprocate in the axial direction, and the conveyance and the suction are continued. Thereby the thrombus T can be removed relatively quickly. At this time, because the suction force acts on the inlet of the cutting unit 40, the cut thrombus T can be sucked while being prevented as much as possible from escaping.

After completion of the cutting, conveyance, and suction of the thrombus T, the rotary motion of the driven shaft 20 is stopped. Next, the medical device 10 is extracted from the blood vessel. The treatment is thereby completed.

As described above, the medical device 10 according to the first embodiment is a medical device 10 for removing a thrombus T (object) within a blood vessel (living body lumen), the medical device 10 including: the rotatable tubular driven shaft 20 having the leading-out hole 24 opening in a proximal portion of the driven shaft 20; the cutting unit 40 disposed on the distal side of the driven shaft 20, the cutting unit 40 cutting the thrombus T while rotating together with the driven shaft 20; and the suction tubular body 70 having a distal portion and a proximal portion; the distal portion of the suction tubular body 70 being located within the driven shaft 20, and the proximal portion of the suction tubular body 70 being located outside the driven shaft 20 and extending in a direction of separating from the driven shaft 20 outward in a radial direction of the driven shaft 20. In the medical device 10 configured as described above, the proximal portion of the suction tubular body 70 whirls when the driven shaft 20 is rotated to rotate the cutting unit 40. Thereby, a centrifugal force directed outward in the radial direction of the rotating driven shaft 20 acts on matter within the proximal portion of the suction tubular body 70, and a suction force directed to the proximal side occurs within the suction tubular body 70. Therefore, the thrombus T can be conveyed by making the suction force act on the inside of the driven shaft 20 using the rotation of the driven shaft 20 that rotates the cutting unit 40. Thus, the thrombus T within the blood vessel can be removed effectively.

The medical device 10 further includes the operation unit 60 including the housing space 61 that houses the portion provided with the leading-out hole 24 in the driven shaft 20 and the suction tubular body 70 led out from the leading-out hole 24, wherein the operation unit 60 has the suction hole 67 that allows a suction force to act externally on the housing space 61. Thus, when the suction force is made to act from the suction hole 67, the suction force can be made to act on the proximal side opening portion 73 of the suction tubular body 70 whirling within the operation unit 60.

In addition, the leading-out hole 24 is located in a side portion of the driven shaft 20. Thus, the suction tubular body 70 can be rather easily led out from the driven shaft 20 to the outside in the radial direction of the driven shaft 20.

In addition, the suction tubular body 70 rotates together with the driven shaft 20. Thus, the proximal portion of the suction tubular body 70 whirls when the driven shaft 20 is rotated. Therefore, a centrifugal force directed outward in the radial direction of the rotating driven shaft 20 acts on the matter within the proximal portion of the suction tubular body 70, and a suction force directed to the proximal side occurs within the suction tubular body 70.

In addition, the driven shaft 20 includes the tubular driven tube 21 and the spiral conveying body 22 provided to the inner surface of the driven tube 21. Thus, when the driven shaft 20 is rotated, the conveying body 22 can produce a force act on the thrombus T in the lumen of the driven shaft 20, and convey the thrombus T to the proximal side or in the proximal direction. At this time, a relatively wide space is secured inside the spiral conveying body 22. The conveying body 22 can therefore make the force act on the thrombus T without hindering the suction force acting from the suction tubular body 70.

The medical device 10 further includes the long resistor 50 having a sectional shape that is a non-perfect circle or non-circle (e.g., rectangle), the resistor 50 being disposed in the lumen of the driven shaft 20 and rotatable relative to the driven shaft 20. Thus, the thrombus T in the lumen of the driven shaft 20 can be moved in a desirable direction along the resistor 50 when the conveying body 22 is rotated while the resistor 50 suppresses the rotation of the thrombus T cut by the cutting unit 40 and guided into the lumen of the driven shaft 20. At this time, because the cross section of the resistor 50 is a non-perfect circle or non-circle (e.g., rectangle), a wide space can be secured between the resistor 50 and the conveying body 22 while the rotation of the thrombus T is suppressed. Therefore, a relatively large amount of thrombus T can be conveyed quickly through the lumen of the driven shaft 20, so that the thrombus T within the blood vessel can be removed effectively. Further, because a wide space can be secured between the conveying body 22 and the resistor 50, the suction force of the suction tubular body 70 is not hindered, and both the conveying force of the conveying body 22 and the suction force can be made to act effectively on the thrombus T.

In addition, the driven shaft 20 has the slits penetrating from an inner surface to an external surface. Thus, while the slits impart flexibility to the driven shaft 20, the suction tubular body 70 in the lumen of the driven shaft 20 prevents a negative pressure from escaping from the slits, so that the suction force can be maintained.

In addition, the suction tubular body 70 gradually separates from the driven shaft 20 toward the proximal side. That is, the proximal portion of the suction tubular body 70 is angled relative to the driven shaft 20 (central axis of the driven shaft 20) so that the proximal portion of the suction tubular body 70 gradually moves farther and farther away from the driven shaft 20. Thus, a large amount of matter on which the centrifugal force acts can be housed within the proximal portion of the suction tubular body 70. The suction force occurring in the suction tubular body 70 can therefore be enhanced.

In addition, the operation unit 60 has the first seal portion 63 sliding on the outer circumferential surface of the driven shaft 20. Thus, the negative pressure within the housing space 61 can be maintained.

The present disclosure also provides a treatment method for removing a thrombus T (object) in a lesioned part within a blood vessel (living body lumen) using the medical device 10 described above. The treatment method includes: inserting the medical device 10 into the blood vessel; cutting the thrombus T within the blood vessel while rotating the cutting unit 40 by the driven shaft 20, and guiding the cut thrombus T into the lumen of the driven shaft 20; sucking the thrombus T within the driven shaft 20 by generating a suction force by the suction tubular body 70 rotating together with the driven shaft 20; and extracting the medical device 10 from within the blood vessel. The treatment method configured as described above can make the suction force act on the inside of the driven shaft 20 by the centrifugal force generated in the matter within the suction tubular body 70 by rotating the driven shaft 20 to rotate the cutting unit 40. Therefore, the thrombus T within the blood vessel can be removed effectively by the suction force using the rotation of the driven shaft 20 that rotates the cutting unit 40.

Second Embodiment

Figure 11:
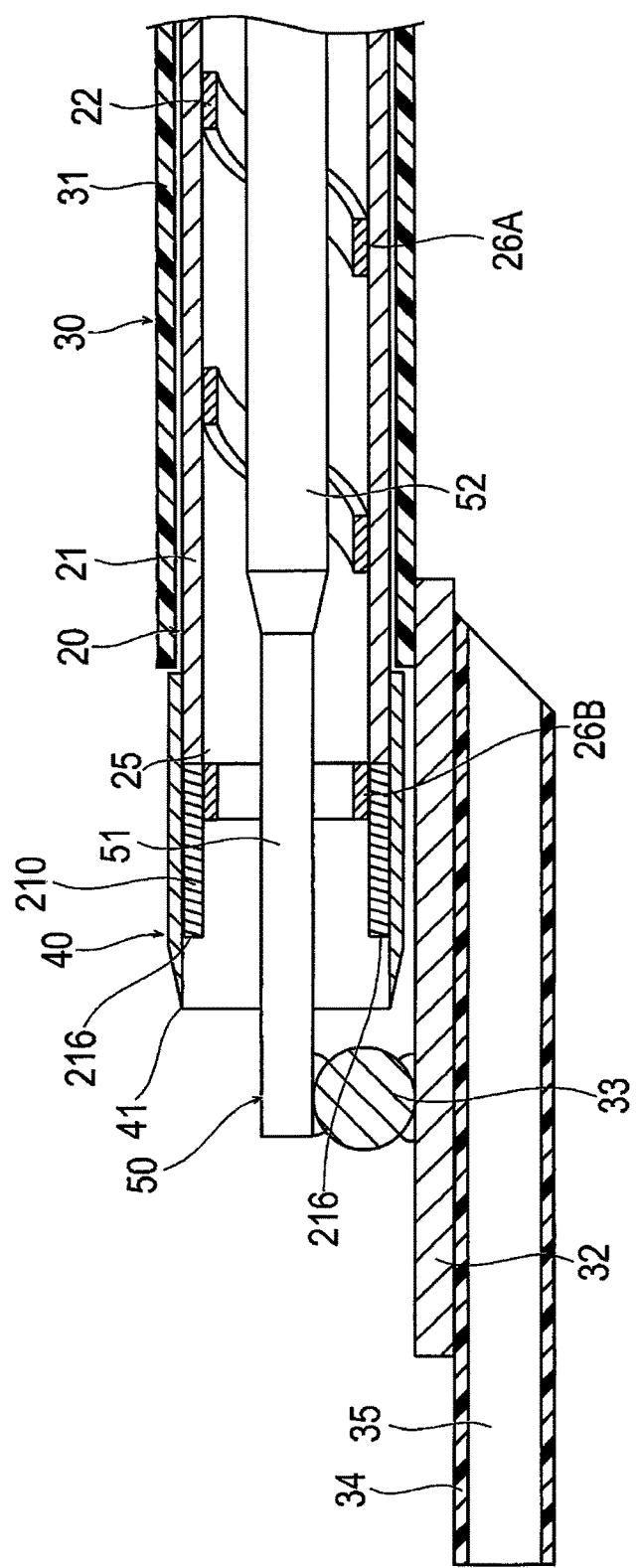
FIG. 11 is a sectional view illustrating a distal portion of a medical device according to a second embodiment.
Figure 12:
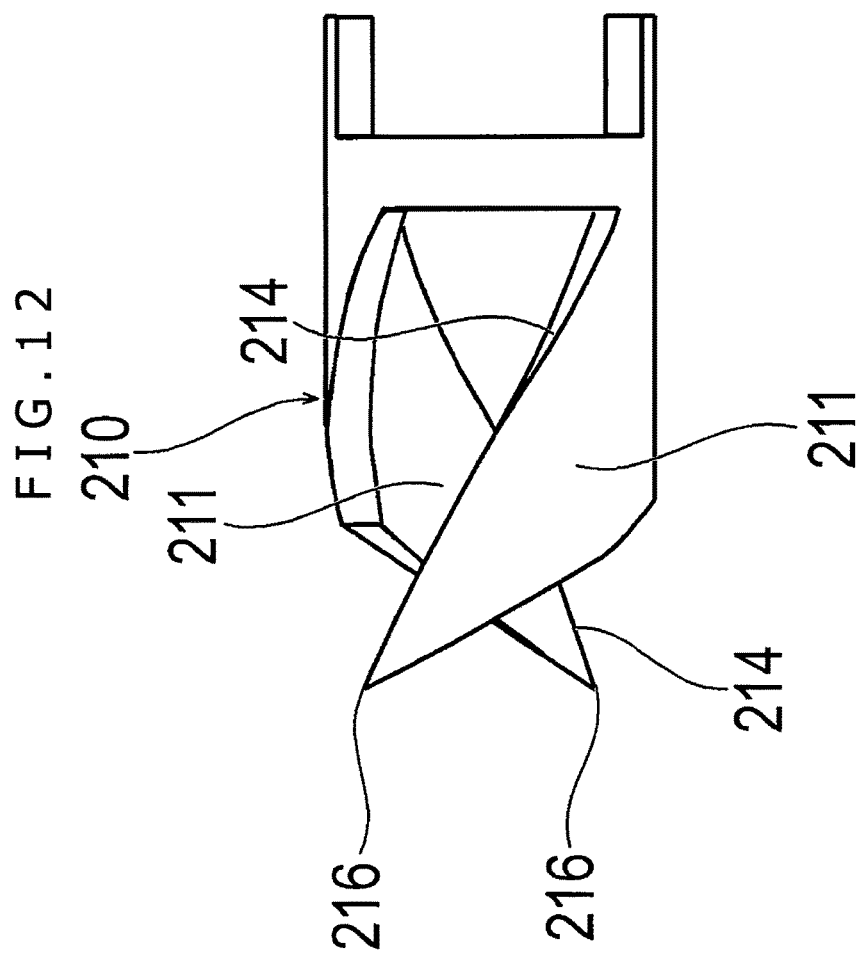
FIG. 12 is a plan view illustrating a second cutting unit of the medical device according to the second embodiment.

A medical device according to a second embodiment is illustrated in FIGS. 11 and 12 and differs from the medical device 10 according to the first embodiment only in that the medical device according to the second embodiment is provided with a second cutting unit 210. Parts of the medical device that are similar to or have functions similar to those in the first embodiment are identified by the same reference symbols, and a detailed description of such features is not repeated.

As illustrated in FIGS. 11 and 12, the second cutting unit 210 is fixed to the outer circumferential surface of the distal side ring portion 26B of the first conveying body 26. The second cutting unit 210 has two spiral cutting blades 211. The two cutting blades 211 have shapes rotationally symmetric with respect to the central axis of the first conveying body 26. The two cutting blades 211 each have a first end surface 214 inclined at a same angle as (or a different angle from) that of the spiral portion 26A of the first conveying body 26.

Second edges 216 of the second cutting unit 210 are inclined with respect to the central axis of the first conveying body 26. The second edges 216 can therefore bite into the thrombus T and cut away the thrombus T by rotating. The second cutting unit 210 is therefore different from the cutting unit 40 that functions to cut off the thrombus T by being pushed in to the distal side. The cutting unit 40 cuts off the thrombus T by being pushed in. The cutting unit 40 can therefore cut off a large amount of relatively soft thrombus T. On the other hand, the second cutting unit 210 cuts away the thrombus T by a rotational force, and can therefore destroy a hard thrombus T. When the medical device is thus provided with both the cutting unit 40 and the second cutting unit 210, the medical device can cut various (different) thrombi T.

In addition, because the second cutting unit 210 has the spiral first end surfaces 214, the second cutting unit 210 can smoothly guide the cut thrombus T to the first conveying body 26. When the inclination angle of the first end surfaces 214 is equal to the inclination angle of the spiral of the first conveying body 26, the thrombus T can be guided to the first conveying body 26 more smoothly. Hence, the second cutting unit 210 functions also as a conveying body. Because the second cutting unit 210 functions also as a conveying body, the second cutting unit 210 has an effect even without the second edges 216 for cutting the thrombus T.

In addition, the second cutting unit 210 is located in a gap between the outer circumferential surface of the first conveying body 26 and the inner circumferential surface of the cutting unit 40. Therefore, as compared with the case where the second cutting unit 210 is not provided, it is relatively easy for the thrombus T to enter the inside of the first conveying body 26 smoothly.

As described above, the medical device according to the second embodiment has the second cutting unit 210 disposed inside the cutting unit 40 (first cutting unit). Thus, the thrombus T can be cut by the cutting unit 40 and the second cutting unit 210 having different characteristics. Various thrombi T different in characteristics such as material, hardness, viscosity, shape, and the like can therefore be cut excellently by one (the same) device.

In addition, the second cutting unit 210 has the second edges 216 that cut the thrombus T in a rotational direction by rotating. Thus, because the second cutting unit 210 cuts the thrombus T by a rotational force, a high cutting force can be generated as compared with the case where cutting is performed by pushing in. Therefore, even a hard thrombus T, for example, can be cut effectively by the second cutting unit 210.

In addition, the second edges 216 of the second cutting unit 210 are located more to the proximal side than the edge 41 of the first cutting unit 40 (i.e., the second edges 216 of the second cutting unit 210 are proximal of the edge 41 of the first cutting unit 40). Thus, the thrombus T that can be cut by pushing in is quickly cut by the first cutting unit 40, and the thrombus T cut by the cutting unit 40 can be cut finely by the rotating second cutting unit 210. The thrombus T can therefore be made to enter the lumen of the driven shaft 20 easily.

Third Embodiment

Figure 13:
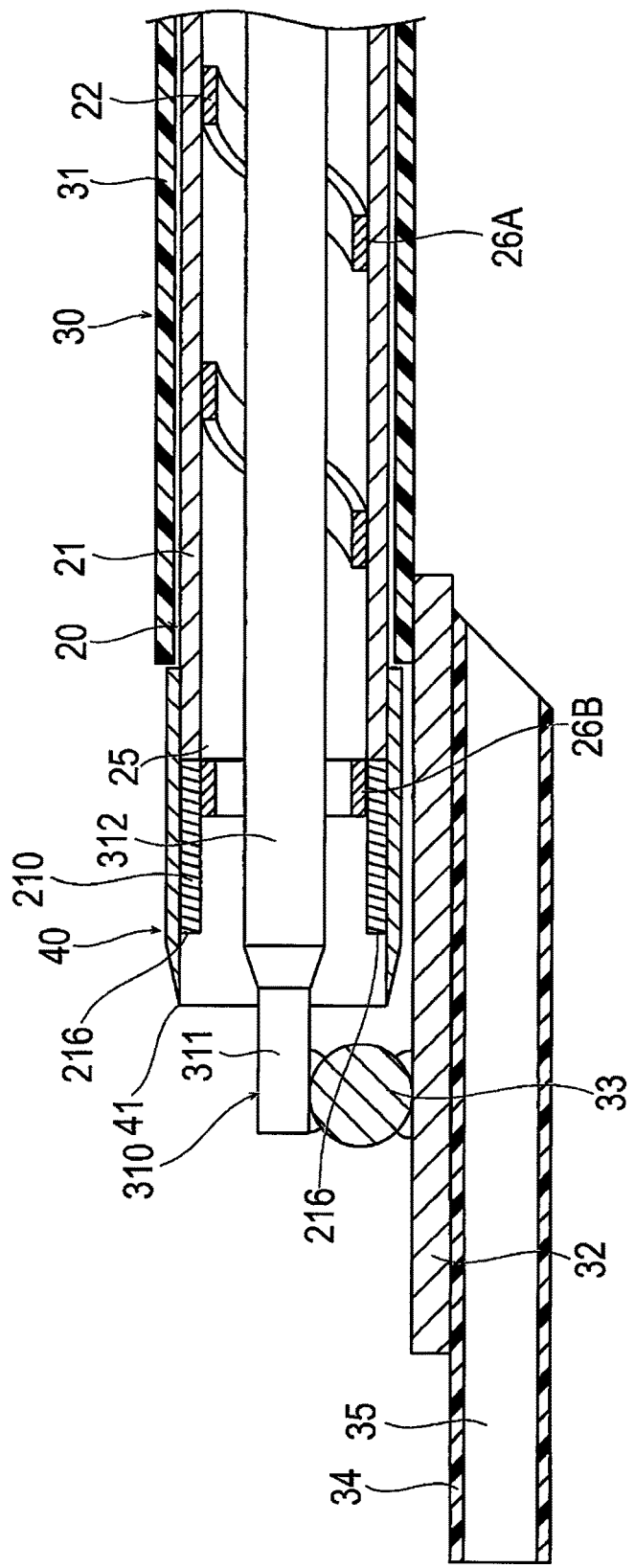
FIG. 13 is a sectional view illustrating a distal portion of a medical device according to a third embodiment.

A medical device according to a third embodiment is illustrated in FIG. 13 and differs from the medical device according to the second embodiment only in terms of the structure of a resistor 310. Parts of the medical device that are similar to or have functions similar to those in the first and second embodiments are identified by the same reference symbols, and a detailed description of such features is not repeated.

In the third embodiment, as illustrated in FIG. 13, the resistor 310 includes a first resistor 311 having a perfect circle as its cross sectional shape, which cross section is perpendicular to the central axis of the resistor 310. The first resistor 311 is located distal of the distal end of the second cutting unit 210. The resistor 310 also includes a second resistor 312 having a non-perfect circle as the shape of its cross section, which cross section is perpendicular to the central axis. The second resistor 312 extends proximally of the edge 41 of the first cutting unit 40 and distally of the distal end of the second edges 216 of the second cutting unit 210. Thus, the distal end of the second resistor extends distally at least as far as the distal end of the second edges 216 of the second cutting unit 210, and may extend distally beyond the distal end of the second edges 216 of the second cutting unit 210 as shown in FIG. 13. Therefore, the second resistor 312 that suppresses the rotation of the thrombus T is located entirely inside the second cutting unit 210. Because the second cutting unit 210 cuts the thrombus T by a rotational force, the thrombus T can be cut excellently when the rotation of the thrombus T within the second cutting unit 210 is suppressed. In addition, because the second cutting unit 210 is also a conveying body having the spiral first end surfaces 214, the thrombus T can be smoothly guided into the lumen of the driven tube 21 when the rotation of the thrombus T inside the second cutting unit 210 is suppressed by the second resistor 312.

Fourth Embodiment

Figure 14:
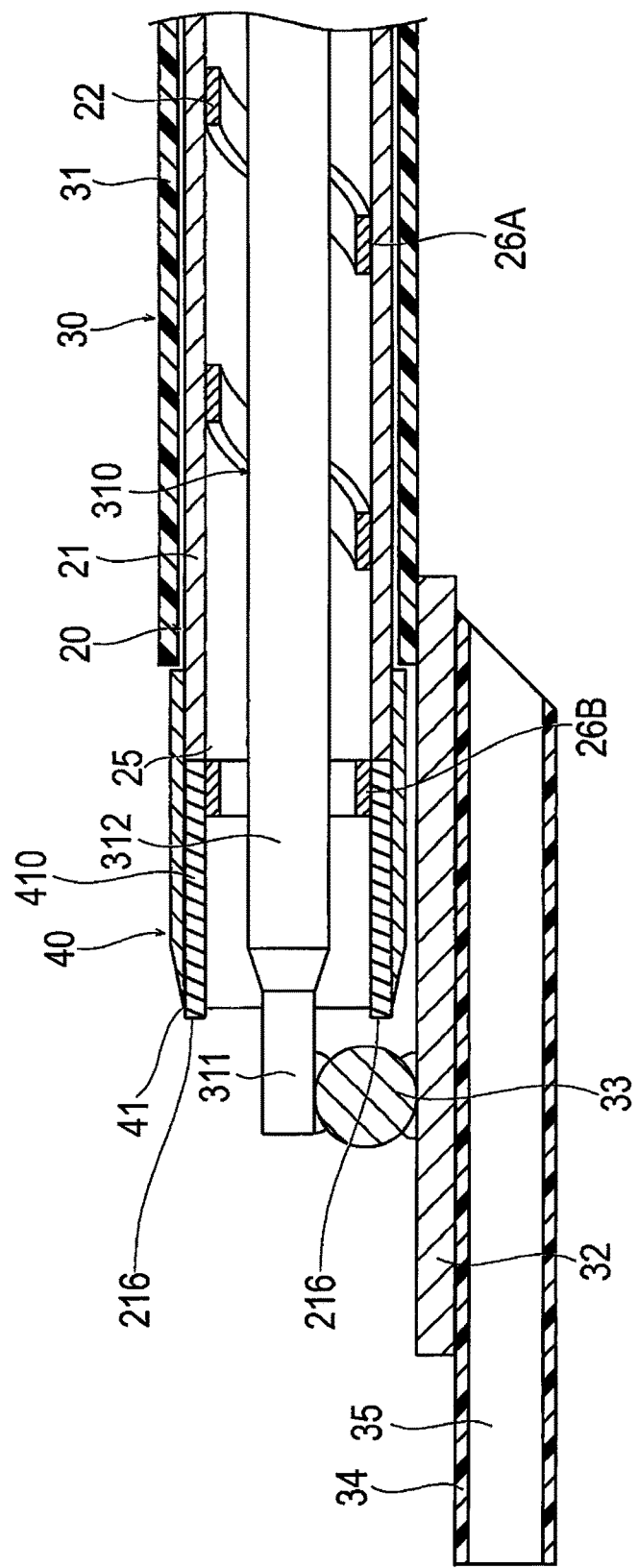
FIG. 14 is a sectional view illustrating a distal portion of a medical device according to a fourth embodiment.

A medical device according to a fourth embodiment is illustrated in FIG. 14 and differs from the medical device according to the third embodiment only in terms of the length in the axial direction of a second cutting unit 410. Parts of the medical device that are similar to or have functions similar to those in the first to third embodiments are identified by the same reference symbols, and a detailed description of such features is not repeated.

In the fourth embodiment, as illustrated in FIG. 14, the second edges 216 located on a most distal side of the second cutting unit 410 are located distal to the distally located edge 41 of the cutting unit 40. The second cutting unit 410 can therefore effectively cut the thrombus T before being cut by the cutting unit 40. Therefore, a hard thrombus T can be effectively cut by the second cutting unit 410 and guided into the driven tube 21. Hence, the medical device according to the fourth embodiment is effective in a case where there are many relatively hard thrombi T. The position of the second edges 216 of the second cutting unit 410 may be the same in the axial direction as the position of the edge 41 of the cutting unit 40. That is, the distal-most second edges 216 of the second cutting unit 410 and the distal-most edge 41 of the cutting unit 40 may be at the same axial position. In this embodiment, the medical device is configured so that both the first cutting unit 40 and the second cutting unit 410 act on the thrombus T simultaneously, and can therefore cut various thrombi T in a well-balanced manner.

In the fourth embodiment, the second edges 216 of the second cutting unit 410 are located more to the distal side than the edge 41 of the cutting unit 40 (first cutting unit). Thus, the thrombus T can be cut by the rotating second cutting unit 410 before being cut by the cutting unit 40. A thrombus T that is difficult to cut merely by pushing in can therefore be cut effectively by the second cutting unit 410. Therefore, various thrombi T including hard thrombi, for example, can be cut in a well-balanced manner.

Fifth Embodiment

Figure 15:
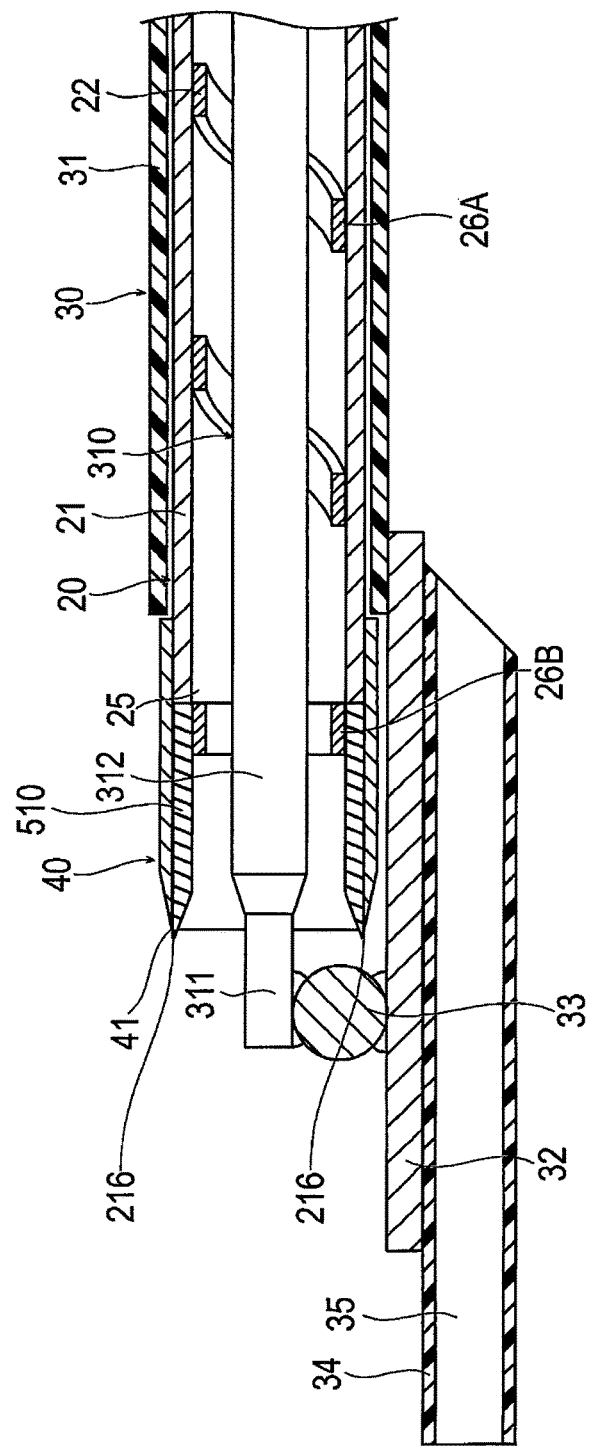
FIG. 15 is a sectional view illustrating a distal portion of a medical device according to a fifth embodiment.

A medical device according to a fifth embodiment is illustrated in FIG. 15 and differs from the medical device according to the fourth embodiment only in terms of the shape of a second cutting unit 510. Parts of the medical device that are similar to or have functions similar to those in the first to fourth embodiments are identified by the same reference symbols, and a detailed description of such features is not repeated.

In the fifth embodiment, as illustrated in FIG. 15, the inside diameter of the distal end portion of the second cutting unit 510 is increased in a tapered manner so that the inner diameter increases in the distal direction. That is, the second edges 216 of the second cutting unit 510 are thinned toward the distal end or in the distal direction. Therefore, a cutting force received by the thrombus T entering the inside of the second cutting unit 510 is gradually increased toward the proximal side of the second cutting unit 510. Hence, the thrombus T can be smoothly guided with a small resistance to the inside of the second cutting unit 510 and the first cutting unit 40.

The present disclosure is not limited to the foregoing embodiments alone, but can be variously changed by those skilled in the art within technical ideas of the present disclosure. For example, the living body lumen into which the medical device is inserted is not limited to a blood vessel, but may, for example, be a vessel, a ureter, a bile duct, an oviduct, a hepatic duct, or the like. Hence, the object to be destroyed may not be limited to a thrombus.

Figure 16:
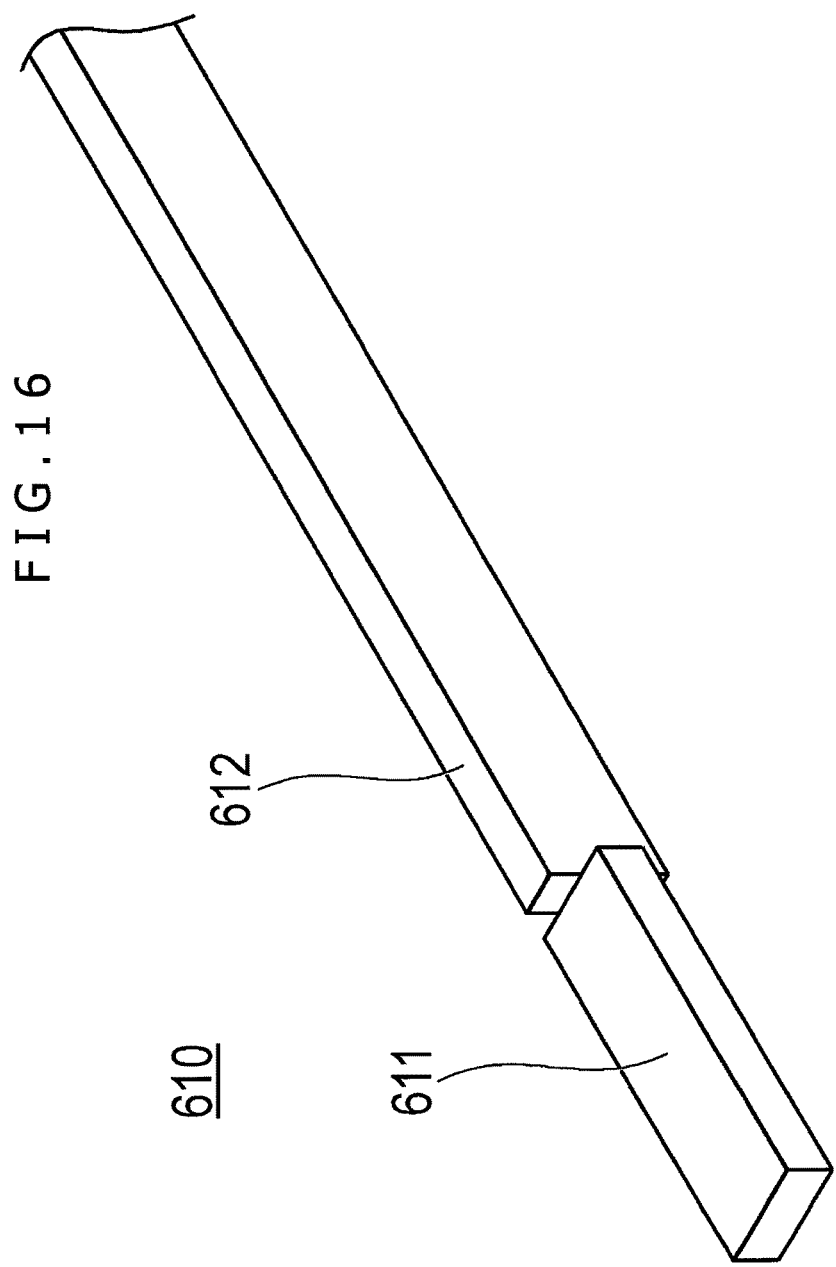
FIG. 16 is a perspective view illustrating a modification of a resistor.

In addition, the resistor may not have a part (axial section) having a perfect circle as the shape of its cross section, which cross section is perpendicular to the central axis. For example, as in a modification illustrated in FIG. 16, the shapes of the cross sections of a first resistor 611 and a second resistor 612 of a resistor 610, which cross sections are perpendicular to the central axis of the respective resistors 611, 612, may each be a rectangle, and the long axes of the respective cross sections may be orthogonal to each other so that the two cross-sections are the same, but are rotationally displaced or offset by 90°.

Figure 17:
FIG. 17 is a sectional view illustrating another modification of the resistor.

In addition, as in another modification illustrated in FIG. 17, a resistor 710 may be twisted. The rotational direction of the twist is the same as the rotational direction of the spiral of the conveying body, but may be different from the rotational direction of the spiral of the conveying body. The pitch distance of the twist is desirably longer than the pitch distance of the conveying body. The thrombus T that receives a rotational force from the conveying body can therefore be conveyed in the axial direction while being allowed to escape somewhat in the rotational direction along the resistor 710. Consequently, the force can be efficiently transmitted to the thrombus T, and the thrombus T can be conveyed through an optimum route.

Figure 18:
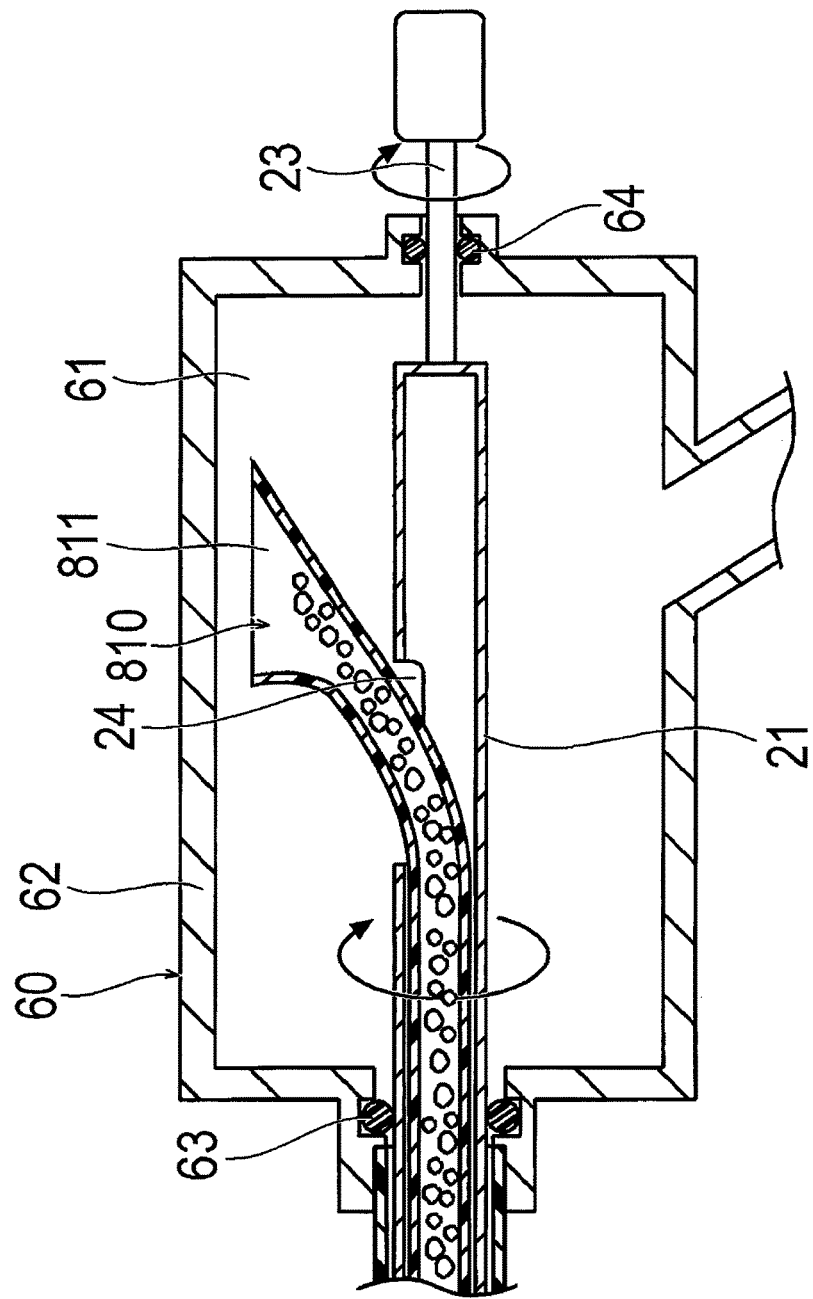
FIG. 18 is a sectional view illustrating a modification of a suction tubular body.

In addition, as in a modification illustrated in FIG. 18, a suction tubular body 810 (proximal end portion of the suction tubular body 810) may be widened in a tapered shape so that the internal cross-sectional area of the proximal end portion of the suction tubular body 810 increases toward a proximal side opening portion 811. The suction tubular body 810 extends toward the proximal side opening portion 811 located on the outside in the radial direction of the driven shaft 20. Thus, a relatively large amount of fluid can be housed within a proximal portion of the suction tubular body 810 which proximal portion has a relatively large radius of gyration and on which a strong centrifugal force acts. A suction force occurring in the suction tubular body 810 can therefore be increased.

Figure 19:
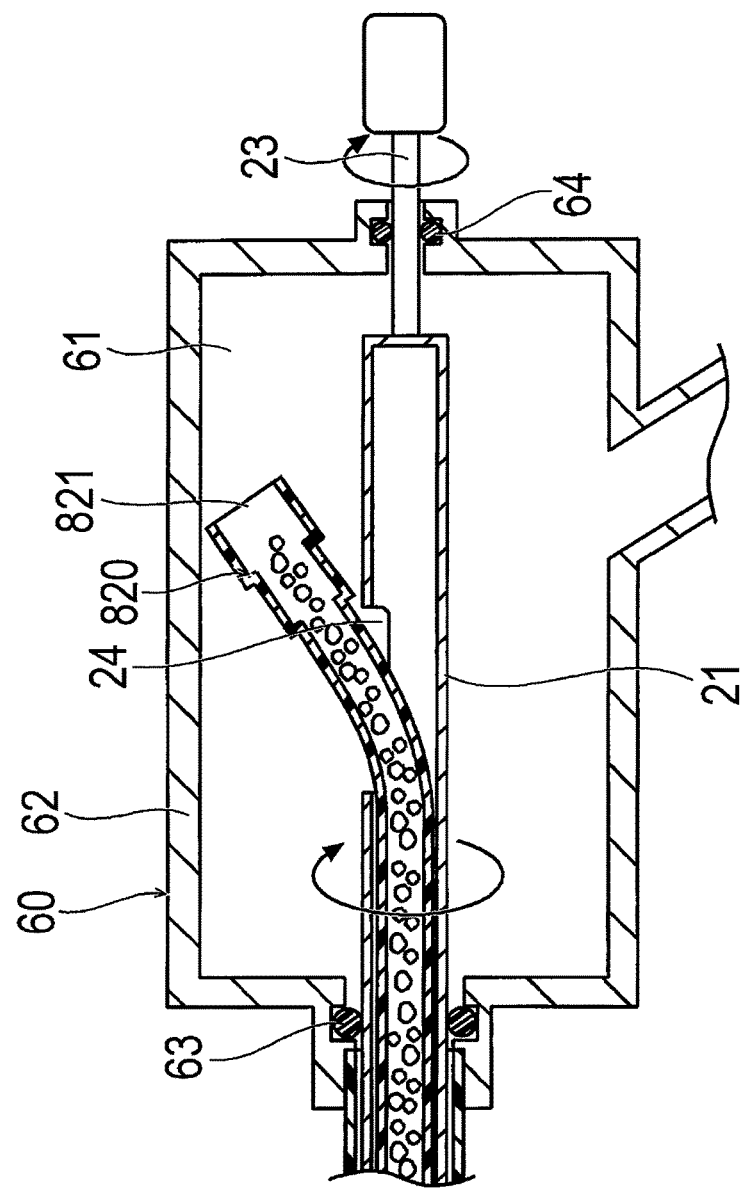
FIG. 19 is a sectional view illustrating another modification of the suction tubular body.

In addition, as in another modification illustrated in FIG. 19, a suction tubular body 820 (proximal end portion of the suction tubular body 820) may be widened stepwise so that the internal cross-sectional area of the proximal end portion of the suction tubular body 820 increases in a stepwise manner toward a proximal side opening portion 821. The suction tubular body 820 extends toward the proximal side opening portion 821 located on the outside in the radial direction of the driven shaft 20. Thus, a relatively large amount of fluid can be housed within a proximal portion of the suction tubular body 820 which proximal portion has a relatively large radius of gyration and on which proximal portion a strong centrifugal force acts. A suction force occurring in the suction tubular body 820 can therefore be increased.

Figure 20:
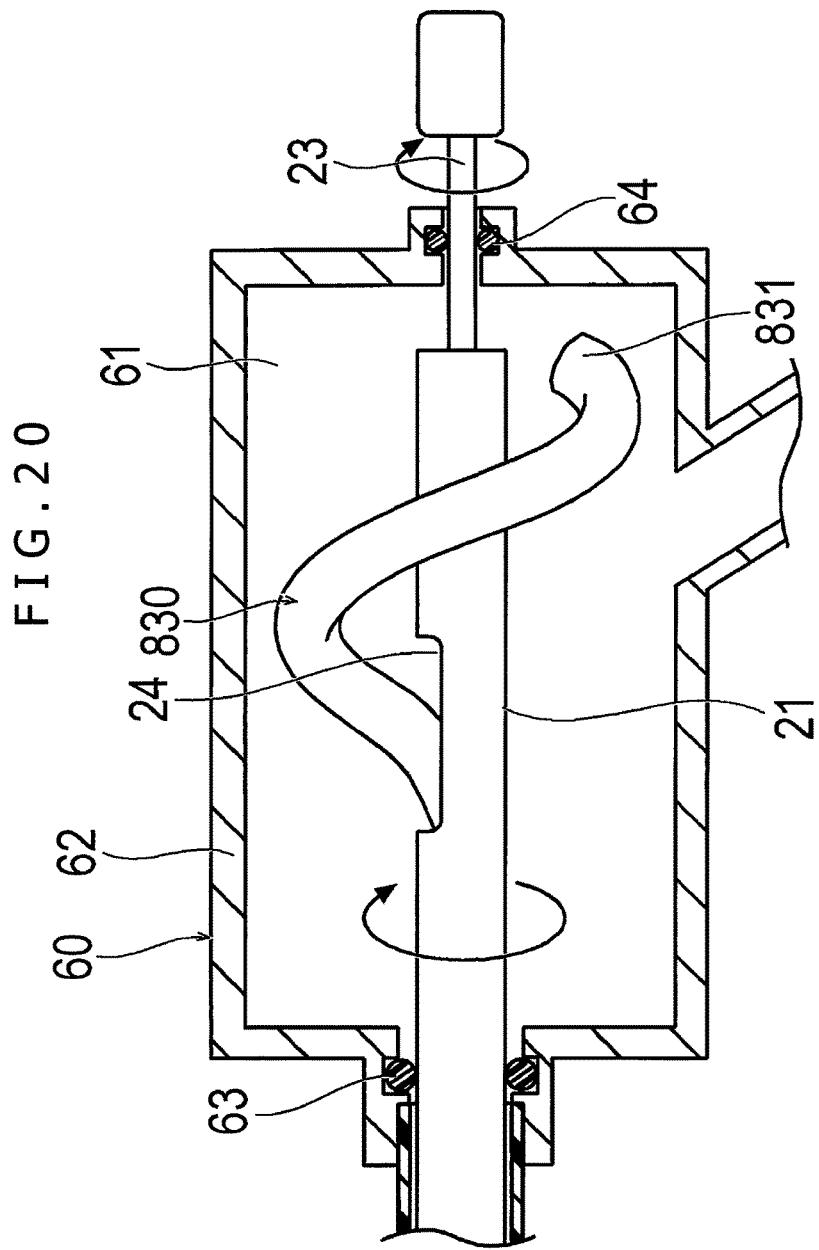
FIG. 20 is a sectional view illustrating yet another modification of the suction tubular body.

In addition, as in yet another modification illustrated in FIG. 20, a suction tubular body 830 may extend to a proximal side opening portion 831 in a spiral manner toward the proximal side. That is, the proximal end part of the suction tubular body 830 may exhibit a spiral shape. The suction tubular body 830 extends in a spiral manner toward the proximal end while being spaced away from the central axis of the driven shaft 20 to the outside in the radial direction of the driven shaft 20. A direction in which the spiral is wound toward the proximal side is an opposite direction from the rotational direction of the driven shaft 20. Thus, when the suction tubular body 830 is rotated together with the driven shaft 20, a fluid within the suction tubular body 830 receives a centrifugal force, and receives a force that extrudes the fluid from an inner wall surface of the suction tubular body 830 to the proximal side. Thereby a suction force occurring in the suction tubular body 830 can be increased.

In addition, the leading-out hole of the driven tube from which hole the suction tubular body is led out may not be the side hole provided in the side surface of the driven tube, but may be, for example, an opening portion provided in the distal side end portion of the driven tube.

In addition, while the conveying body 22 in the foregoing embodiments includes the first conveying body 26 and the second conveying body 27, the conveying body 22 may include only one of the first conveying body 26 and the second conveying body 27. In addition, the conveying body may include one or more other conveying bodies different from the first conveying body 26 and the second conveying body 27.

In addition, the shape of the cross section of the resistor which cross section is perpendicular to the central axis of the resistor is not particularly limited as long as the shape is a non-perfect circle or a non-circle. The non-perfect circle or non-circle shape of the cross section of the resistor may be, for example, an ellipse, a triangle, or a polygon having four angles or more.

The detailed description above describes embodiments of a medical device and a treatment method for cutting an object from an inner wall surface of a living body lumen. These embodiments represent examples of the inventive medical device and a treatment method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device for removing an object within a living body lumen, the medical device comprising: a rotatable tubular driven shaft having a longitudinal axis and configured to rotate around the longitudinal axis, the rotatable tubular driven shaft having a proximal portion, a distal portion and a lumen extending therethrough, wherein the proximal portion of the rotatable tubular driven shaft includes a leading-out hole and is connected to a motor proximal to the leading-out hole; a cutting unit disposed at the distal portion of the rotatable tubular driven shaft, is wherein the cutting unit is rotatable around the longitudinal axis together with the rotatable tubular driven shaft to cut the object; and a suction tubular body having a distal portion, a proximal portion and a lumen extending therethough, the suction tubular body located distal to the motor, wherein the lumen of the distal portion of the suction tubular body communicates with the lumen of the rotatable tubular drive shaft such that the object cut by the cutting unit travels along a conveyance path from the lumen of the rotatable tubular driven shaft to the lumen of the distal portion of the suction tubular body and out of the proximal portion of the suction tubular body, wherein the conveyance path along which the object travels passes through the leading out-hole; and wherein a proximal end of the proximal portion of the suction tubular body extends in a radial direction away from the longitudinal axis such that the proximal end does not axially overlap with a proximal end of the proximal portion of the rotatable tubular drive shaft.

2. The medical device according to claim 1, further comprising: an operation unit including a housing space that houses the proximal portion of the rotatable tubular driven shaft and the proximal portion of the suction tubular body, wherein a part of the suction tubular body passes through the leading-out hole; and
wherein the operation unit includes a suction hole connectable to a syringe to produce a negative pressure in the housing space.

3. The medical device according to claim 1, wherein the leading-out hole is located in a side portion of the rotatable tubular driven shaft.

4. The medical device according to claim 1, wherein the suction tubular body rotates together with the rotatable tubular driven shaft.

5. The medical device according to claim 1, wherein the proximal portion of the suction tubular body extends in a direction angled relative angled relative to the rotatable tubular driven shaft such that the proximal portion of the suction tubular body separates at progressively greater distances from the rotatable tubular driven shaft toward an open proximal end of the suction tubular body.

6. The medical device according to claim 1, wherein the proximal portion of the suction tubular body is widened such that an internal cross-sectional area of the proximal portion of the suction tubular body increases toward a proximal side opening portion of the suction tubular body.

7. The medical device according to claim 1, wherein the motor generates a rotation force around a rotation axis, and the rotation axis of the motor is arranged to be coaxial to the longitudinal axis of the rotatable tubular driven shaft at the proximal portion of the rotatable tubular driven shaft such that a connecting section is located between the proximal portion of the rotatable tubular driven shaft and the motor, wherein the suction tubular body branches from the longitudinal axis at the connecting section to radially extend in the radial direction away from the longitudinal axis.

8. A medical device for removing an object within a living body lumen, the medical device comprising: a driven shaft configured to be connected to a driving unit to rotate the driven shaft, the driven shaft including an interior communicating with an open distal end of the driven shaft and an open proximal end of the driven shaft, the driven shaft including a leading-out hole passing through the driven shaft to communicate the interior of the driven shaft to an exterior of the driven shaft, the leading-out hole being spaced distally from the open proximal end of the driven shaft; a suction tubular body comprising a distal portion, a proximal portion, an open distal end and an open proximal end; the distal portion of the suction tubular body being located within the interior of the driven shaft; a part of the suction tubular body passing through the leading-out hole such that the proximal portion of the suction tubular body is positioned outside of the driven shaft, the proximal portion of the suction tubular body extending in a direction is angled relative to the driven shaft such that the proximal portion of the suction tubular body separates at progressively greater distances from the driven shaft toward the open proximal end of the suction tubular body;
the open distal end of the suction tubular body communicating with the interior of the driven shaft; and the suction tubular body being rotatable to create a suction force in an interior of the suction tubular body that communicates with the interior of the driven shaft by way of the open distal end of the suction tubular body such that the suction force draws the object into the interior of the driven shaft.

9. The medical device according to claim 8, further comprising a rotatably driven cutting unit positioned in the interior of the driven shaft.

10. The medical device according to claim 8, further comprising a cutting unit fixed to the driven shaft such that the cutting unit and the driven shaft rotate together as a unit.

11. The medical device according to claim 8, wherein the driven shaft comprises a driven tube and a helical conveying body fixed to the driven tube such that the helical conveying body rotates together with the driven tube and causes the object drawn into the interior of the driven shaft to move toward the open proximal end of the driven shaft.

12. The medical device according to claim 8, further comprising an operation unit including a housing space in which the open proximal end of the driven shaft and the open proximal end of the suction tubular body is located.

13. The medical device according to claim 8, wherein the operation unit includes a suction hole connectable to a syringe to produce a negative pressure in the housing space.

14. The medical device according to claim 8, wherein the driven shaft comprises a driven tube and a helical conveying body fixed to the driven tube such that the helical conveying body rotates together with the driven tube to cause the object drawn into the interior of the driven shaft to move toward the open proximal end of the driven shaft, the helical conveying body being comprised of a first helical conveying portion and a second helical conveying portion each having a respective pitch distance, the pitch distance of the first conveying portion being different from the pitch distance of the second conveying portion, wherein the pitch distance is an axial distance between adjacent windings.

15. A medical device for removing an object within a living body lumen, the medical device comprising: a rotatable tubular driven shaft having a longitudinal axis and a proximal portion, the rotatable tubular driven shaft having an interior; a cutting unit disposed at the distal portion of the rotatable tubular driven shaft and rotatable together with the rotatable tubular driven shaft to cut the object; a suction tubular body having a longitudinal axis, a proximal-most end, a proximal-most end portion that includes the proximal-most end, and a distal portion; the suction tubular body including an interior that communicates with the interior of the rotatable tubular driven shaft such that parts of the object cut by the cutting unit enter the interior of the rotatable tubular driven shaft and are drawn into the interior of the suction tubular body; a casing surrounding an internal housing space, the proximal-most end portion of the suction tubular body being located in the internal housing space of the casing, and the proximal portion of the rotatable tubular driven shaft being located in the internal housing space of the casing; and a part of the proximal-most end portion of the suction tubular body located in the internal housing space of the casing positioned completely outside the interior of the proximal portion of the rotatable tubular driven shaft located in the internal housing space of the casing such that the longitudinal axis of the part of the proximal-most end portion of the suction tubular body is not coaxial with the longitudinal axis of the proximal portion of the rotatable tubular driven shaft located in the internal housing space of the casing.

16. The medical device according to claim 15, further comprising a suction hole that communicates with the internal housing space of the casing and that is connectable to a device configured to create suction in the internal housing space of the casing.

17. The medical device according to claim 15, wherein the part of the proximal-most end portion of the suction tubular body is a first part and a second part of the suction tubular body passes through a hole in a portion of the rotatable tubular driven shaft that is distally spaced from a proximal-most end of the rotatable tubular driven shaft.

18. The medical device according to claim 15, wherein the suction tubular body rotates together with the rotatable tubular driven shaft.

19. The medical device according to claim 15, wherein the part of the proximal-most end portion of the suction tubular body that is located in the internal housing space of the casing and that is positioned completely outside the interior of the proximal portion of the rotatable tubular driven shaft has an increasing internal cross-sectional area.

20. A medical device for removing an object within a living body lumen, the medical device comprising: a rotatable tubular driven shaft configured to be rotatably driven by a motor and having a proximal portion and a distal portion, the proximal portion of the rotatable tubular driven shaft including a leading-out hole, and a proximal end portion of the rotatable tubular driven shaft proximal to the leading-out hole configured to be connected to a motor that rotatably drives the rotatable tubular driven shaft to rotate about an axis, the rotatable tubular driven shaft having an interior; a cutting unit disposed at the distal portion of the rotatable tubular driven shaft and rotatable together with the rotatable tubular driven shaft to cut the object; a suction tubular body having a distal portion and a proximal-most end portion, the suction tubular body including an interior that communicates with the interior of the rotatable tubular driven shaft such that parts of the object cut by the cutting unit enter the interior of the rotatable tubular driven shaft and are drawn into the interior of the suction tubular body, the leading-out hole in the rotatable tubular driven shaft configured as an exit by which the parts of the object cut by the cutting unit are discharged from the interior of the rotatable tubular driven shaft; the proximal-most end portion of the suction tubular body having a central axis and located outside the rotatable tubular driven shaft and extending in a radial direction projecting outward away from the rotatable tubular driven shaft, the proximal-most end portion of the suction tubular body including an internal cross-section defined by a transverse plane passing through the proximal-most end portion of the suction tubular body and perpendicular to the central axis of the proximal-most end portion of the suction tubular body, the rotatable tubular driven shaft, at a point adjacent to and distal of the leading-out hole, including an internal cross-section defined by a transverse plane passing through the rotatable tubular driven shaft and perpendicular to the axis of the rotatable tubular driven shaft;

and the internal cross-section of the suction tubular body being positioned completely radially outside of the internal cross-section of the rotatable tubular driven shaft such that the internal cross-section of the suction tubular body is always located completely radially outside of the internal cross-section of the rotatable tubular driven shaft.

* * * * *